US009629856B2

(12) United States Patent
Dreher

(10) Patent No.: US 9,629,856 B2
(45) Date of Patent: Apr. 25, 2017

(54) COMPOSITIONS AND METHODS FOR THE TREATMENT OF SKIN DISEASES AND DISORDERS USING ANTIMICROBIAL PEPTIDE SEQUESTERING COMPOUNDS

(75) Inventor: Frank Dreher, San Francisco, CA (US)

(73) Assignee: Anteis SA, Plan-les-Ouates (CH)

(*) Notice: Subject to any disclaimer, the term of this patent is extended or adjusted under 35 U.S.C. 154(b) by 442 days.

(21) Appl. No.: 13/038,524

(22) Filed: Mar. 2, 2011

(65) Prior Publication Data

US 2011/0217249 A1    Sep. 8, 2011

Related U.S. Application Data

(60) Provisional application No. 61/310,168, filed on Mar. 3, 2010.

(51) Int. Cl.
| | | |
|---|---|---|
| *A61K 38/20* | (2006.01) | |
| *A61K 38/02* | (2006.01) | |
| *A61P 17/00* | (2006.01) | |
| *A61K 31/765* | (2006.01) | |
| *A61K 31/70* | (2006.01) | |
| *A61P 31/00* | (2006.01) | |
| *A61K 31/66* | (2006.01) | |
| *A61K 9/00* | (2006.01) | |
| *A61K 9/06* | (2006.01) | |
| *A61K 31/522* | (2006.01) | |
| *A61K 31/685* | (2006.01) | |
| *A61K 31/715* | (2006.01) | |
| *A61K 31/716* | (2006.01) | |
| *A61K 31/721* | (2006.01) | |
| *A61K 33/30* | (2006.01) | |
| *A61K 33/34* | (2006.01) | |
| *A61K 36/02* | (2006.01) | |
| *A61K 36/04* | (2006.01) | |
| *A61K 36/33* | (2006.01) | |
| *A61K 36/886* | (2006.01) | |
| *A61K 45/06* | (2006.01) | |
| *A61K 38/00* | (2006.01) | |

(52) U.S. Cl.
CPC ............ *A61K 31/66* (2013.01); *A61K 9/0014* (2013.01); *A61K 9/06* (2013.01); *A61K 31/522* (2013.01); *A61K 31/685* (2013.01); *A61K 31/70* (2013.01); *A61K 31/715* (2013.01); *A61K 31/716* (2013.01); *A61K 31/721* (2013.01); *A61K 33/30* (2013.01); *A61K 33/34* (2013.01); *A61K 36/02* (2013.01); *A61K 36/04* (2013.01); *A61K 36/33* (2013.01); *A61K 36/886* (2013.01); *A61K 45/06* (2013.01); *A61K 38/00* (2013.01)

(58) Field of Classification Search
CPC ............ A61K 2300/00; A61K 38/00; A61K 2800/58; A61K 31/722; A61K 31/727; A61K 31/765; A61K 33/00; A61K 8/97; A61K 35/36; A61K 31/355; A61K 31/66; A61K 31/737; A61K 33/30; A61K 39/395; A61K 9/0014; A61K 9/5036; A61K 31/721; A61K 8/0212; A61K 8/73; A61K 31/726; A61K 31/738; A61K 33/04; A61K 38/17; A61K 47/36; A61K 8/735; A61K 9/06; A61K 9/1075; A61Q 19/08; A61Q 19/00; A61Q 17/00; A61Q 1/12; A01N 2300/00; A01N 31/04; A01N 41/04; A01N 25/10; C07K 14/47; A61L 27/34; A61L 27/20; A61L 31/042; A61L 2300/45; A61L 15/44; A61L 2300/41; A61L 27/54; A61L 31/16
See application file for complete search history.

(56) References Cited

U.S. PATENT DOCUMENTS

| | | | |
|---|---|---|---|
| 2,798,053 A | | 7/1957 | Brown |
| 3,238,100 A | | 3/1966 | Meyer et al. |
| 4,509,949 A | | 4/1985 | Huang et al. |
| 4,599,379 A | | 7/1986 | Flesher et al. |
| 4,628,078 A | | 12/1986 | Glover et al. |
| 4,835,206 A | | 5/1989 | Farrar et al. |
| 4,849,484 A | | 7/1989 | Heard |
| 4,879,282 A | * | 11/1989 | Saliba, Jr. ............... 514/56 |
| 4,912,093 A | | 3/1990 | Michaeli |
| 5,087,445 A | | 2/1992 | Haffey et al. |
| 5,100,660 A | | 3/1992 | Hawe et al. |
| 5,204,414 A | * | 4/1993 | Pelah et al. ............ 525/327.8 |
| 5,872,109 A | * | 2/1999 | Akima ............... A61K 31/737 514/54 |
| 5,908,836 A | * | 6/1999 | Bar-Shalom ........... A61K 8/26 514/23 |

(Continued)

FOREIGN PATENT DOCUMENTS

| | | | |
|---|---|---|---|
| CN | 101282708 A | 10/2008 | |
| DE | EP 1949887 A2 * | 7/2008 | ............ A61K 8/49 |

(Continued)

OTHER PUBLICATIONS

Kenshi et al. Antimicrobial peptides in human skin disease. Eur J Dermatol. 2008 ; 18(1): 11-21.*
Jenssen et al. Peptide Antimicrobial Agents. Clin. Microbiol. Rev. 2006, 19(3):491.*
Gunay et al. Heparinoids: Structure, Biological Activities and Therapeutic Applications. Planta Medica 1999; 65:301-306.*
Margolis et al. Distribution and metabolism of mucopolysaccharides and glycoproteins in neuronal perikarya, astrocytes, and oligodendroglia. Biochemistry. Jul. 2, 1974;13(14):2849-52.*
Temovate E® Prescribing Information. GlaxoSmithKline 2002.*
Tetracycline Product Information. Sigma 2003.*

(Continued)

*Primary Examiner* — Satyanarayana R Gudibande
*Assistant Examiner* — Jia-Hai Lee
(74) *Attorney, Agent, or Firm* — Mintz Levin Cohn Ferris Glovsky and Popeo, P.C.

(57) ABSTRACT

The present invention provides compositions containing one or more antimicrobial peptide sequestering compounds and methods for topical application of such compositions to the skin to treat skin diseases and disorders such as rosacea in humans.

38 Claims, No Drawings

(56) References Cited

U.S. PATENT DOCUMENTS

| | | | |
|---|---|---|---|
| 5,932,215 | A | 8/1999 | de Lacharriere et al. |
| 5,952,372 | A | 9/1999 | McDaniel |
| 6,440,465 | B1* | 8/2002 | Meisner .................. 424/725 |
| 6,444,647 | B1 | 9/2002 | Robinson et al. |
| 6,562,355 | B1* | 5/2003 | Renault ............ A61K 8/0208 424/401 |
| 7,855,187 | B1 | 12/2010 | Prestwich et al. |
| 2002/0037314 | A1* | 3/2002 | Meisner ............ A61K 31/375 424/449 |
| 2006/0246029 | A1* | 11/2006 | Patt ...................... 424/70.14 |
| 2007/0009586 | A1 | 1/2007 | Cohen et al. |
| 2008/0274068 | A1 | 11/2008 | Tanaka et al. |
| 2009/0197308 | A1 | 8/2009 | Liu et al. |
| 2009/0286756 | A1 | 11/2009 | Ciancia et al. |
| 2009/0318534 | A1 | 12/2009 | Gallo et al. |

FOREIGN PATENT DOCUMENTS

| | | |
|---|---|---|
| EP | 0 085 579 A2 | 8/1983 |
| EP | 228868 A2 | 7/1987 |
| EP | 0640346 A1 | 3/1995 |
| EP | 0754460 A1 | 1/1997 |
| EP | 1 402 874 A1 | 3/2004 |
| EP | 2201930 A1 | 6/2010 |
| FR | 2 877 565 A1 | 5/2006 |
| JP | 58-208217 A | 12/1983 |
| JP | 10-502665 A | 3/1998 |
| JP | 56077294 | 11/1998 |
| JP | 2000-178196 A | 6/2000 |
| JP | 2000-515897 A | 11/2000 |
| JP | 2002-512180 A | 4/2002 |
| JP | 2003-505423 A | 2/2003 |
| JP | 2005-060234 A | 3/2005 |
| JP | 2005-508936 A | 4/2005 |
| JP | 2009-143863 A | 7/2009 |
| JP | 2010-534672 A | 11/2010 |
| JP | 2013-500274 A | 1/2013 |
| WO | WO-89/05646 A1 | 6/1989 |
| WO | WO-94/08574 A1 | 4/1994 |
| WO | WO-96/02260 A1 | 2/1996 |
| WO | WO-98/48627 A1 | 11/1998 |
| WO | WO-9848627 A1 | 11/1998 |
| WO | WO-99/53897 A2 | 10/1999 |
| WO | WO-99/53897 A3 | 10/1999 |
| WO | WO-9964469 A1 | 12/1999 |
| WO | WO-01/07057 A1 | 2/2001 |
| WO | WO-02/098372 A1 | 12/2002 |
| WO | WO-03/030813 A2 | 4/2003 |
| WO | WO-03/030813 A3 | 4/2003 |
| WO | WO 2006/028863 A1 * 3/2006 ............ A61F 13/00 | |
| WO | WO-2006111633 A2 | 10/2006 |
| WO | WO-2008047779 A1 | 4/2008 |
| WO | WO-2008/134430 A1 | 11/2008 |
| WO | WO-2009/015183 A1 | 1/2009 |
| WO | WO-2009064412 A1 | 5/2009 |
| WO | WO-2009065116 A1 | 5/2009 |
| WO | WO-2010083368 A2 | 7/2010 |
| WO | WO-2011/011881 A1 | 2/2011 |
| WO | WO-2011/109469 A1 | 9/2011 |

OTHER PUBLICATIONS

Wang et al. Human peptidoglycan recognition proteins require zinc to kill both gram-positive and gram-negative bacteria and are synergistic with antibacterial peptides. J Immunol 2007; 178:3116-3125.*

Andersson et al. Antimicrobial activities of heparin-binding peptides. Eur. J. Biochem. 2004. 271, 1219-1226.*

Lacey et al. Mite-related bacterial antigens stimulate inflammatory cells in rosacea. Br J Dermatol. Sep. 2007;157(3):474-81.*

Kajio et al. Stabilization of basic fibroblast growth factor with dextran sulfate. FEBS Lett. Jul. 20, 1992;306(2-3):243-6.*

Dreno et al. Effect of zinc gluconate on propionibacterium acnes resistance to erythromycin in patients with inflammatory acne: in vitro and in vivo study. Eur J Dermatol. May-Jun. 2005;15(3):152-5.*

Heinze et al. Functional Polymers Based on Dextran. Adv Polym Sci (2006) 205: 199-291.*

Mallbris et al. UVB Upregulates the Antimicrobial Protein hCAP18 mRNA in Human Skin. Journal of Investigative Dermatology (2005) 125, 1072-1074.*

Andersson et al. Antimicrobial activities of heparin-binding peptides. Eur. J. Biochem. 2004; 271:1219-1226.*

Dextran sulfate 10 sodium salt. Amersham Biosciences product instruction 2001.*

Glaser et al. UV-B radiation induces the expression of antimicrobial peptides in human keratinocytes in vitro and in vivo. J Allergy Clin Immunol 2009;123:1117-23.*

Frohm et al. The expression of the gene coding for the antibacterial peptide LL-37 is induced in human keratinocytes during inflammatory disorders. J Biol Chem. Jun. 13, 1997;(24): 15258-63.*

Stallings et al. Practical uses of botanicals in skin care. J Clin Aesthet Dermatol. Jan. 2009;2(1):36-40.*

Cohen et al. Diagnosis and treatment of rosacea. J Am Board Fam Pract. May-Jun. 2002;15(3):214-7.*

Aluminum Acetate Topical Solution (Domeboro, Bluboro, Burow's Solution Operational Medicine 2001.*

Aisa et al., "Fucoidan induces apoptosis of human HS-sultan cells accompanied by activation of caspase-3 and down-regulation of ERK pathways", *Am. J. Hematol.*, 78:7-14 (2005).

Bakunina et al., Degradation of Fucoidan by the Marine Proteobacterium *Pseudoalteromonas citrea:*, *Microbiol.*, 71:41-47 (2002).

Barak et al., "Antimicrobial peptides: effectors of innate immunity in the skin", *Adv. Dermatol.*, 21:357-374 (2005).

Barco et al., "Rosacea", *Actas Dermosifiliogr.*, 99:244-256 (2008).

Beress et al., "A new procedure for the isolation of anti-HIV compounds (polysaccharides and polyphenols) from the marine alga *Fucus vesiculosus*", *J. Nat. Products*, 56:478-488 (1993).

Berteau et al., "Sulfated fucans, fresh perspectives: structures, functions, and biological properties of sulfated fucans and an overview of enzymes active toward this class of polysaccharide", *Glycobiology*, 13:29R-40R (2003).

Bikowski et al., "Rosacea: where are we now?", *J. Drugs Dermatol.*, 3:251-261 (2004).

Bilan et al., "A highly regular fraction of a fucoidan from the brown seaweed *Fucus distichus* L.", *Carbohydr. Res.*, 339:511-517 (2004).

Bilan et al., Polysaccharides of Algae: 60.1 Fucoidan from the Pacific Brown Alga *Analipus japonicus* (Harv.) Winne (Ectocarpales, Scytosiphonaceae), *Russ J. Bioorgan. Chem.*, 33:38-46 (2007).

Bilan et al., "Structure of a fucoidan from the brown seaweed *Fucus serratus* L.", *Carbohydr. Res.*, 341:238-245 (2006).

Bixler et al., "The Carrageenan Connection IV", *Brit. Food J.*, 96:12-17 (1994).

Braff et al., "Antimicrobial peptides: an essential component of the skin defensive barrier", *Curr. Top. Microbiol. Immunol.*, 306:91-110 (2006).

Bucki et al., "Cathelicidin LL-37: a multitask antimicrobial peptide", *Arch. Immunol. Ther. Exp. (Warsz)*, 58:15-25 (2010).

Buechner, "Rosacea: an update", *Dermatology*, 210:100-108 (2005).

Carney et al., "Rosacea: a review of current topical, systemic and light based therapies", Gital Dermatol Venereol, 144:673-88 (2009).

Culp et al., "Rosacea: A review", *P.T.*, 34:38-45 (2009).

Cumashi et al., "A comparative study of the anti-inflammatory, anticoagulant, antiangiogenic, and antiadhesive activities of nine different fucoidans from brown seaweeds", *Glycobiology*, 17:541-552 (2007).

De Clercq, E., "Current lead natural products for the chemotherapy of human immunodeficiency virus (HIV) infection", *Med. Res. Rev.*, 20:323-349 (2000).

Descamps et al., "Isolation and culture of a marine bacterium degrading the sulfated fucans from marine brown algae", *Mar. Biotechnol.*, 8:27-39 (2006).

(56) References Cited

OTHER PUBLICATIONS

Descotes et al., "Clinical immunotoxicity of therapeutic proteins", *Exp. Opin. Drug Metab. Toxicol.*, 4:1537-1549 (2008).
Dobashi et al., "Isolation and preliminary characterization of fucose-containing sulfated polysaccharides with blood-anticoagulant activity from the brown seaweed *Hizikia fusiforme*", *Carbohydr. Res.*, 194:315-320 (1989).
Dombrowski et al., "Control of cutaneous antimicrobial peptides by vitamin D3", *Arch. Dermatol. Res.*, 302:401-408 (2010).
Duarte et al., "Structural studies on fucoidans from the brown seaweed *Sargassum stenophyllum*", *Carbohydr. Res.*, 333:281-293 (2001).
Dupont; "Traitement du psoriasis par la lecithine marine", *Phytotherapie*, 1:15-22 (2006).
Durr et al., "LL-37, the only human member of the cathelicidin family of antimicrobial peptides", *Biochim. Biophys. Acta*, 758:1408-1425 (2006).
Guarrera et al., "Flushing in rosacea: a possible mechanism", *Arch. Dermatol. Res.*, 272:311-316 (1982).
Harder et al., "Enhanced expression and secretion of antimicrobial peptides in atopic dermatitis and after superficial skin injury", *J. Invest. Dermatol.*, 130:1355-1364 (2010).
Hata et al., "Antimicrobial peptides, skin infections, and atopic dermatitis", *Semin. Cutan. Med. Surg.*, 27:144-150 (2008).
Holtkamp et al., "Fucoidans and fucoidanases—focus on techniques for molecular structure elucidation and modification of marine polysaccharides", *Appl. Microbiol. Biotechnol.*, 82:1-11 (2009).
Jackson et al., "A randomized, investigator-blinded trial to assess the antimicrobial efficacy of a benzoyl peroxide 5%/ clindamycin phosphate 1% gel compared with a clindamycin phosphate 1.2%/ tretinoin 0.025% gel in the topical treatment of acne vulgaris", *J. Drugs Dermatol.*, 9:131-136 (2010).
Jhamandas et al., "Fucoidan inhibits cellular and neurotoxic effects of beta-amyloid (A beta) in rat cholinergic basal forebrain neurons", *Eur. J. Neurosci.*, 21:2649-2659 (2005).
Knutsen, et al., "A Modified System of Nomenclature for Red Algal Galactans", *Bot. Mar.*, 37:163-169 (1994).
Kuberan et al., "Chemoenzymatic synthesis of classical and non-classical anticoagulant heparan sulfate polysaccharides", *J. Biol. Chem.*, 278:52613-52621 (2003).
Kuberan et al., "Enzymatic synthesis of antithrombin III-binding heparan sulfate pentasaccharide", *Nat. Biotechnol.*, 21:1343-1346 (2003).
Kuberan et al., "Rapid two-step synthesis of mitrin from heparosan: a replacement for heparin", *J. Am. Chem. Soc.*, 125:12424-12425 (2003).
Kuznetsova et al., "Anticoagulant activity of fucoidan from brown algae *Fucus evanescens* of the Okhotsk Sea", *Bull. Exp. Biol. Med., translation of Byulleten Eksperimental'noi Biologii i Meditsiny*, 136:471-473 (2003).
Lahaye, "Developments on gelling algal galactans, their structure and physico-chemistry",*J. Appl. Phycol.*, 13:173-184 (2001).
Li et al., "Fucoidan: structure and bioactivity", *Molecules*, 13:1671-1695 (2008).
Li et al., "Structural investigation of a fucoidan containing a fucose-free core from the brown seaweed, *Hizikia fusiforme*", *Carbohydr. Res.*, 341:1135-1146 (2006).
Maaroufi et al., "Influence of the oversulfation method and the degree of sulfation on the anticoagulant properties of dermatan sulfate derivatives", *Thromb. Res.*, 59:749-758 (1990).
Metz-Boutique et al., "Antimicrobial peptides present in mammalian skin and gut are multifunctional defence molecules", *Curr. Pharm. Des.*, 16:1024-1039 (2010).
Mulloy et al., "Sulfated fucans from echinoderms have a regular tetrasaccharide repeating unit defined by specific patterns of sulfation at the 0-2 and 0-4 positions", *J. Biol. Chem.*, 269: 22113-22123 (1994).

Niyonsaba et al., "Human defensins and cathelicidins in the skin: beyond direct antimicrobial properties", *Crit. Rev. Immunol.*, 26:545-576 (2006).
Obluchinskahya et al., "Development of Extraction Technology and Characterization of Extract from Wrack Algae Grist", *Pharm. Chem. J.*, 38:323-326 (2004).
Pereira et al., "Structure and anticoagulant activity of a sulfated galactan from the red alga, *Gelidium crinale*. Is there a specific structural requirement for the anticoagulant action?", *Carbohydr. Res.*, 340:2015-2023 (2005).
Peric et al., *Dtsch. Med. Wochenschr.*, 134:35-38 (2009).
Perry et al., "Preoperative and Postoperative Dynamic Electromyography as an Aid in Planning Tendon Transfers in Children with Celebral Palsy", *Carbohydr. Res.*, 59:531-537 (1977).
Petitou et al., "A synthetic antithrombin III binding pentasaccharide is now a drug! What comes next?", *Angew. Chem. Int. Ed.*, 43 3118-3133 (2004).
Plewig et al., "Acne and Rosacea", p. 435, 2nd ed., (1993).
Pomin et al., "Structure, biology, evolution, and medical importance of sulfated fucans and galactans", *Glycobiology*, 18(12):1016-1027 (2008).
Qiu et al., "Effect of oversulfation on the chemical and biological properties of fucoidan", *Carbohydr. Polym.*, 63:224-228 (2006).
Reviers et al., "Essai D'Interpretation De La Structure Des Fucoidanes En Liaison Avec Leur Localisation Dans La Paroi Des Pheophycees", *Cryptogam. Algol.*, 4:55-62 (1983).
Ribeiro et al., "A sulfated alpha-L-fucan from sea cucumber", *Carbohydr. Res.*, 255:225-240 (1994).
Sakai et al., "A marine strain of flavobacteriaceae utilizes brown seaweed fucoidan", *Mar. Biotechnol.*, 4:399-405 (2002).
Schauber et al., "Antimicrobial peptides and the skin immune defense system", *J. Allergy Clin. Immunol.*, 122:261-266 (2008).
Schauber et al., *Hautarzt*, 59:72-74 (2008).
Scheinfeld et al., "A review of the diagnosis and treatment of rosacea", *Postgrad. Med.*, 122:139-143 (2010).
Schittek et al., "The role of antimicrobial peptides in human skin and in skin infectious diseases", *Infectious Disorders Drug Targets*, 8:135-143 (2008).
Signore, R. J., "A pilot study of 5 percent permethrin cream versus 0.75 percent metronidazole gel in acne rosacea", *Cutis*, 56:177-179 (1995).
Suppiramaniam et al., "Modulatory Effects of Dextran Sulfate and Fucoidan on Binding and Channel Properties of AMPA Receptors Isolated from Rat Brain", *Synapse*,, 60:456-464 (2006).
Takano et al., "Sulfation of Polysaccharides with Sulfuric Acid Mediated by Dicyclohexylcarbodimide", *J. Carbohydr. Chem.*, 15:449-457 (1996).
Tako, et al., "Chemical Characterization of Acetyl Fucoidan and Alginate from Commercially Cultured Cladosiphon okamuranus", *Bot. Mar.*, 43:393-398 (2000).
Toida et al., "Structure and Bioactivity of Sulfated Polysaccharides", *Trends Glycoscience Glycotechnology*, 15:29-46 (2003).
Usov, "Structural analysis of red seaweed galactans of agar and carrageenan groups", *Food Hydrocolloids*, 12:301-308 (1998).
Van Zuuren et al., "Systematic review of rosacea treatments", *J. Am. Acad. Dermatol.*, 56:107-115 (2007).
Vilela-Silva et al., "Structure of the sulfated alpha-L-fucan from the egg jelly coat of the sea urchin *Strongylocentrotus franciscanus*: patterns of preferential 2-O- and 4-O-sulfation determine sperm cell recognition", *Glycobiology*, 9:927-933 (1999).
Webster, "Rosacea", *Med. Clin. North Am.*, 93:1183-1194 (2009).
Gilbert et al. "Efficacy and Tolerance of a Topical Skin Care Regimen as an Adjunct to Treatment of Facial Rosacea." *Cosmet. Dermatol.* 21.9(2008):501-504.
Bellavia, A. et al. (Jun. 1987). "Effects of Dextran Sulphate on Lymphoblast Extravasation into Inflammatory Skin Sites," *Immunopharmacology* 13(3):173-180.
Takenaka, I. (1969). "Effects of the Ester of Dextran Sulfate (MDS-KOWA) on Psoriasis Vulgaris," *Iryo* [*Medicament*] 23(3):343-347 (English Translation of Abstract only).

* cited by examiner

COMPOSITIONS AND METHODS FOR THE TREATMENT OF SKIN DISEASES AND DISORDERS USING ANTIMICROBIAL PEPTIDE SEQUESTERING COMPOUNDS

RELATED APPLICATIONS

This application claims priority to U.S. Ser. No. 61/310,168, filed on Mar. 3, 2010, which is herein incorporated by reference in its entirety.

FIELD OF THE INVENTION

The invention relates generally to compositions containing one or more antimicrobial peptide sequestering compounds and methods for topical application to the skin to treat skin diseases and disorders, such as rosacea in humans.

BACKGROUND OF THE INVENTION

Rosacea is a common but poorly understood disorder of the facial skin that is estimated to affect well over 14 million Americans. Rosacea is characterized by flushing, erythema, papules, pustules, telangiectasia, facial edema, ocular lesions, and, in its most advanced and severe form, hyperplasia of tissue and sebaceous glands leading to rhinophyma. It may appear as redness, prominent spider-like blood vessels, swelling, or skin eruptions similar to acne. Rhinophyma, a florid overgrowth of the tip of the nose with hypervascularity and modularity, is an unusual progression of rosacea of unknown cause. Ocular lesions are common, including mild conjunctivitis, burning, and grittiness. Blepharitis, the most common ocular manifestation, is a non-ulcerative condition of the lid margins. One typically distinguishes between four common subtypes: (I) erythematotelangiectatic rosacea, (II) papulopustular rosacea, (III) phymatous rosacea, and (IV) ocular rosacea.

Flushing and the regulatory mechanism of the blood vessels are of importance in the pathogenesis of rosacea. The stages associated with flushing progress from episodes of flushing to persistent telangiectases. Telangiectasia, the dilation of capillaries and small blood vessels, has been studied using infrared photography and results have indicated, consistent with a previously developed theory that the color change in rosacea (i.e. skin appears red; also described as redness) is due to the dilation of the non-muscular endothelial capillaries and venules.

The symptoms of rosacea are exacerbated by sun exposure, hot weather, immersion in hot water, high humidity, sweating, exercise, emotional stress, spicy food, vasodilating stimuli, alcoholic beverages.

While the cause of rosacea is poorly understood, numerous theories have been offered. For example, such hypotheses have included gastrointestinal, psychological, infectious, climatic, and immunological causes. One commonly proposed etiologic theory is based on the presence of *Demodex folliculorum* mites in patients with rosacea. This organism feeds on sebum, and, in some cases, treatments of *Demodex* infestation have led to improvements in the rosacea. However, in a review of biopsies, *Demodex folliculorum* was noted in only few of the specimens. Likewise, a bacterial cause for the disease has also been hypothesized, but consistent findings of one bacteria have yet to be demonstrated.

Although climate, specifically exposure to extremes of sun and cold, may have an effect on the course of the disease, the exact role of climate is not clear. Similarly, while an autoimmune process has been suggested, and tissue fixed immunoglobulins have been reported in patients with chronic inflammation of rosacea, no other evidence has been found. Some other experimental evidence has suggested that rosacea may represent a type of hypersensitivity reaction.

Thus, as no single hypothesis appears to adequately explain both the vascular changes and the inflammatory reaction seen in patients with rosacea, the pathogenesis of this disease is unclear.

Rosacea and rosacea treatments and potential therapies have been extensively described in numerous review articles such as Scheinfeld et al., A review of the diagnosis and treatment of rosacea. Postgrad Med 122:139-43 (2010); Webster, Rosacea. Med. Clin North Am 93:1183-94 (2009); Kennedy Carney et al., Rosacea: a review of current topical, systemic and light-based therapies. G Ital Dermatol Venereol 144: 673-88 (2009); Culp et al., Rosacea: A review. P&T 34:38-45 (2009); Barco et al., Rosacea. Actas Dermosifiliogr 99: 244-56 (2008); Van Zuuren et al., Systematic review of rosacea treatments. J Am Acad Dermatol 56:107-15 (2007); Buechner, Rosacea: an update. Dermatology 210:100-108 (2005); and Bikowski et al., Rosacea: where are we now? J Drugs Dermatol 3:251-261 (2004).

Currently, treatment for rosacea can be orally or topically applied antibiotics (such as tetracycline, clindamycin, erythromycin), as well as vitamin A, salicylic acid, zinc oxide, antifungal agents, or steroids. Another known treatment for rosacea is metronidazole (an antiprotozoal and antibacterial agent) and permethrin (a pyrethroid), alone or with oral 13-cis-retinoic acid (isotretinoin). (See Signore, Cutis, 56: 177-79 (1995)). Metronidazole, however, has been reported as ineffective against skin redness, telangiectases and flushing.

Drugs useful for inhibiting flushing include, for example, methysergide, indomethacin, clonidine, aspirin, promethazine, propranolol, diazepam, and cimetidine. (See Guarrera, et al., Arch Dermatol Res, 272:311-16 (1982)). In addition, U.S. Pat. No. 5,952,372 discloses a method of treating rosacea with oral or topical use of ivermectin, and U.S. Pat. No. 5,932,215 discloses the use of Calcitonin Gene Related Peptide (CGRP), a substance P antagonist, in compositions to treat skin redness in discrete erythema and rosacea.

Frequently, the skin of a patient suffering from rosacea is hypersensitive, and therefore, the treatment for rosacea is or feels particularly irritating to the skin. In fact, most patients with rosacea complain of sensitive skin that stings, burns, and itches after application of treatment compositions, cosmetics, fragrances, or sunscreens because their facial skin is unusually vulnerable to chemical and physical stimuli. (See Plewig, G. and Kligman, A. M., "Acne and Rosacea", p. 435 (2d ed. 1993)). Soaps, alcoholic cleansers, tinctures and astringents, abrasives and peeling agents are all potential irritants and should be avoided.

Therefore, reducing irritation associated with compositions designed to treat rosacea is a special problem. Even more difficult to treat, is the irritation experienced when treating the skin for rosacea complexed with acne vulgaris. Typically, products are formulated to be free of irritating ingredients such as actives, surfactants emulsifiers, and fragrances. However, when this approach is taken, there can be a compromise in the efficacy of the ingredients with respect to their desired activity.

Accordingly, there is a need for compositions suitable for topical application and methods for treating this disease that are efficient, well-tolerated or non-irritating, are stable, and do not cause an acnegenic/comedogenic response. The compositions and methods of the present invention address these long felt needs in the art.

SUMMARY OF THE INVENTION

Provided herein are methods for treating skin diseases and disorders associated with deregulation of the skin's antimicrobial peptide formation, processing, or both by administering an effective amount of one or more (e.g., 1, 2, 3, 4, 5, 6, 7, 8, or more) antimicrobial peptide sequestering compounds to a patient suffering from the skin disease or disorder. Also provided are compositions containing one or more antimicrobial peptide sequestering compounds for use in treating skin diseases and disorders associated with deregulation of the skin's antimicrobial peptide formation, processing, or both. In any of these methods or compositions for use, the skin diseases and disorders associated with deregulation of the skin's antimicrobial peptide formation, processing or both, can include, but are not limited to, rosacea, psoriasis, acne, atopic dermatitis, seborrheic dermatitis, skin cancers such as melanoma, skin wounds, and ulcers. Those skilled in the art will recognize that the methods and compositions for use of the invention can be used to treat any skin diseases and disorders where individuals suffering from the disease or disorder have abnormal levels or concentrations of antimicrobial peptides in skin or on skin surface as compared to normal skin.

The antimicrobial peptide being sequestered by the one or more antimicrobial peptide sequestering compounds may be a cationic antimicrobial peptide; a cationic antimicrobial peptide that has been proteolyic processed by endogenous proteases present in the skin, the eccrine sweat glands, the hair bulb and sebocytes, in sweat and sebum, or on the surface of the skin; or any combination thereof.

In one preferred embodiment, the antimicrobial peptide being sequestered by the compound is a human, cationic antimicrobial peptide. Examples of suitable human, cationic antimicrobial peptides include, but are not limited to human cathelicidin polypeptides (e.g., hCAP18, LL-37), human defensin polypeptides (e.g., alpha defensins, beta-defensins (e.g., beta-defensin 1, beta-defensin 2, beta-defensin 3)), and/or human dermcidin polypeptides. In some preferred embodiments, the cathelicidin is hCAP18. In another preferred embodiment, the cathelicidin is LL-37. In another preferred embodiment, the cathelicidin is LL-37 and/or hCAP18 that has been proteolytic processed by endogeneous proteases present in the skin or on the skin surface. Antimicrobial peptides such as the cathelicidins, defensins, and dermicidins and their formation and metabolism in humans have been described in several review articles including Dombrowski et al., Arch Dermatol Res, 302: 401-08 (2010); Metz-Boutigue et al., Curr Pharm Des, 16: 1024-1039 (2010); Bucki et al., Arch Immunol Ther Exp (Warsz), 58:15-25 (2010); Peric et al., Dtsch Med Wochenschr, 134: 35-38 (2009); Hata et al., Semin Cutan Med Surg, 27:144-150 (2008); Schittek et al., Infectious Disorders—Drug Targets 8:135-43 (2008); Schauber et al., J Allergy Clin Immunol, 122: 261-266 (2008); Schauber et al., Hautarzt, 59: 72-74 (2008); Braff et al., Curr Top Microbiol Immunol, 306: 91-110 (2006); Dürr et al., Biochim Biophys Acta, 758:1408-1425 (2006); Niyonsaba et al., Crit. Rev Immunol, 26: 545-576 (2006); Barak et al., Adv Dermatol, 21: 357-374 (2005). As of today, over 20 human antimicrobial peptides have been identified in human skin and sweat; more human antimicrobial peptides will likely be discovered in skin in the future.

Preferably, the antimicrobial peptide sequestering compound is not a poly-amino acid, a peptide, a polypeptide, a protein, an immune-conjugate, or an antibody. Likewise, according to the present invention, the antimicrobial peptide sequestering compound does not inhibit the formation of the antimicrobial peptide. Moreover, the compound used in the methods and compositions of the invention is not a antimicrobial peptide (i.e., cathelicidin) activity or expression inhibitor and does not function by inhibiting serine protease activity and/or expression or by reducing transcription and/or translation of a antimicrobial peptide (i.e., cathelicidin) polynucleotide. Similarly, suitable antimicrobial peptide sequestering compounds for use herein also do not degrade antimicrobial peptides (i.e., cathelicidin polypeptides) into inactive peptides. Moreover, as used herein, the antimicrobial peptide sequestering compound is not a Vitamin D3 antagonist or vitamin D receptor inhibitor Rather, in any of the compositions for use and methods disclosed herein, the human, cationic antimicrobial peptide sequestering compound is an anionic chemical that sequesters or binds the human, cationic antimicrobial peptide by electrostatic interactions. For example, the anionic chemical may include one or more of the following counter ions: ions of alkali metal (e.g., Li, Na, K, etc.), alkaline earth metal (e.g., Ca, Mg, Ba, etc.), transition metal (e.g., Zn, Cu, Zr, Ti, Bi, Mn); ammonium ions ($NH_4^+$); quarternary ammonium cations; and/or the protonated forms of carbohydrates or derivatives of carbohydrates with an amine group. Alternatively (or additionally), the anionic chemical is preferably an anionic polymer other than a poly-amino acid (i.e., peptide, polypeptide, protein).

Examples of suitable anionic polymers can include, but are not limited to, sulfated or polysulfated monosaccharides, and salts and complexes thereof; sulfated or polysulfated disaccharides, and salts and complexes thereof; sulfated or polysulfated polysaccharides, and salts and complexes thereof; a dextran sulfate (e.g., dextran sodium sulfate), and salts and complexes thereof; chondroitin sulfate, and salts and complexes thereof; pentosan polysulfate, and salts and complexes thereof; sucrose sulfate (e.g., any sucrose sulfate such as sucrose octasulphate other than aluminum sucrose sulfate), and salts and complexes thereof; a fucoidan (e.g., an algae extract or an algae extract which has been processed), and salts and complexes thereof; a sulfated galactan, and salts and complexes thereof; a carrageenans (e.g., *Chondrus Crispus*), and salts and complexes thereof; starch sulfate, and salts and complexes thereof; cellulose sulfate, and salts and complexes thereof; a sulfated glycosaminoglycan, and salts and complexes thereof; a heparin; a heparan sulfate; sulfated glucan; and/or any combination(s) thereof.

Those skilled in the art will recognize that the desired anionic polymer can be obtained by preparing sulfated or polysulfated polysaccharides by chemical and/or enzymatic synthesis, and salts and complexes thereof.

The antimicrobial peptide sequestering compound can a plant extract, an algae extract, an aloe vera (barbadensis) extract, a cactus extract, or a shark or fish cartilage extract.

Likewise, the antimicrobial peptide sequestering compound can be a sulfated or polysulfated polymer (e.g., poly(vinyl sulfate), poly(anethole sulfonate)).

The antimicrobial peptide sequestering compound can also be a polymeric sulfonic acid. By way of non-limiting example, one suitable polymeric sulfonic acid that can be used in the methods and compositions for use described herein are hydrophobically modified polymeric sulfonic acids such as Aristoflex® HMP (also called ammonium acryloyldimethyltaurate/beheneth-25 methacrylate crosspolymer; manufactured by Clariant). Another suitable polymeric sulfonic acid that can be used in the methods and compositions described herein is Aristoflex® AVC (also called ammonium acryloyldimethyltaurate/VP copolymer; manufactured by Clariant).

Alternatively (or additionally), the antimicrobial peptide sequestering compound can be a phosphate (e.g., a glycerol phosphate such as sodium glycerophosphate) or a polyphosphate (e.g., a monosaccharide phosphate, a disaccharide phosphate, a polysaccharide phosphate, a glycerophosphate salt (i.e., sodium glycerophosphate), or a starch phosphate). Suitable examples of starch phosphates include, but are not limited to hydroxypropyl starch phosphates (i.e., Structure XL (National Starch, LCC)).

In some embodiments, the antimicrobial peptide sequestering compound can be a phospholipid such as phosphatidylcholine or lecithin.

In other embodiments, the antimicrobial peptide sequestering compound can be a carboxylate, a polyhydroxy acid, hyaluronic acid, alginate, and/or polylactic acid.

Those skilled in the art will recognize that any suitable combination(s) of the antimicrobial peptide sequestering compounds described herein can be used in the methods and compositions for use of the instant invention. Determining which one or more antimicrobial peptide sequestering compounds to use is within the routine level of skill in the art.

Preferably, the antimicrobial peptide sequestering is an anionic chemical that is of a molecular weight of at least 100 g per mol (preferably between 100 to 100,000 g per mol; more preferably between 100 to 25,000 g per mol; most preferably between 100 to 10,000 g per mol).

In any of the methods or compositions for use described herein, the antimicrobial peptide sequestering compound may further bind to or sequester the heparin binding growth factors and/or cytokines, including, but not limited to fibroblast growth factors (e.g., bFGF), vascular endothelial growth factors, and the like.

Preferably, the one or more antimicrobial peptide sequestering compounds that are used in the methods and compositions for use described herein are formulated such that they are suitable for topical application or administration. Thus, the compositions described herein are stable, cosmetically elegant, and well tolerated on subjects affected by the said skin disease and disorder. By way of non-limiting example, the compositions described herein can be formulated as a solution, suspension, gel, hydrogel, cream, emulsion, microemulsion, nano-emulsion, lotion, spray, ointment, patch, tissue cloth, wipe, soap, paste, aerosol, and mask suitable for topical use.

The antimicrobial peptide sequestering compound can be incorporated into these topical formulations in an amount between 0.01 w % to its limit of solubility. For example, the one or more antimicrobial peptide sequestering compounds are incorporated into a topical formulation in an amount between 0.01 w5 to 25 w %. Preferably, the amount of the antimicrobial peptide sequestering compound is between 0.05 w % and 25 w %.

The one or more antimicrobial peptide sequestering compounds used in the methods and compositions for use of the instant invention should be substantially free of cationic polymers including, but not limited to, chitosan, DEAE-dextran, cationic guar gum, cationic polysaccharides (e.g., cationic celluloses), cationic copolymers of saccharides and synthetic cationic monomers, cationic polyakylene imines, and cationic ethoxy polyalkylene imines. Likewise, the compositions should also be substantially free of aluminum or aluminum ions.

The methods described herein can also involve administration of one or more additional compounds or active ingredients. Likewise, the compositions for use of the invention can also include one or more additional compounds or active ingredients. By way of non-limiting example, these additional compounds or active ingredients may include, but are not limited to, rosacea inhibitory agents (e.g., metronidazole, sulfacetamide, sodium sulfacetamide, sulfur, dapson, doxycycline, minocycline, clindamycin, clindamycin phosphate, erythromycin, tetracylclines, azelaic acid, calcium dobesilate, maleic acid, and any compatible combinations thereof); α-adrenergic receptor agonists (e.g., clonidine, amphetamine, doxtroamphetamine, apraclonidine, dipivefrin, α-methyldopa, oxymetazoline, oxymetazoline hydrochloride, methoxamine, metaraminol, medetomidine, dexmedetomidine, ethylnorepinephrine, guanfacine, guanabenz, phenylephrine, phenylephrine hydrochloride, ephedrine, epinine, epinephrine, ethylnorepinephrine, levarterenol, lofexidine, norepinephrine, norphenylephrine, norephedrine, phenylpropanolamine, pemoline, propylhexadrine, pseudoephedrine, methamphetamine, α-methylnorepinephrine, methylphenidate, mephentermine, midodrine, mivazerol, moxonidine, desglymidodrine, tetrahydrozoline, tetrahydrozoline hydrochloride, cirazoline, amidephrine, brimonidine, brimonidine tartrate, naphazoline, isoproterenol, xylazine, xylometazoline, and/or tizanidine); chemicals and botanical extracts with vasoconstrictor properties including, but not limited to, corticosteroids, ephedrine, pseudoephedrine, caffeine, and/or escin; ephedra, phedra sinica, hamamelis viginiana, hydrastis canadensis, lycopus virginicus, aspidosperma quebracho, cytisus scoparius, raphanus sativus linn (radish leave extracts), horse chestnut extracts, etc., as well as any compatible combinations thereof; and/or a nasal and/or sinus decongestant.

Additional examples can include chemicals or botanical extracts with anti-inflammatory properties (e.g., corticosteroids (for short term use)), non-steroidal anti-inflammatory drugs, linoleic acid, linolenic acid, bisabolol, glycyrrhetinic acid, glycerin, plant extracts with anti-inflammatory properties (i.e., tea extracts, chamomile extracts), anti-inflammatory interleukins (e.g., Il-1ra); isoprenylcystein analogues (i.e., N-acetyl-S-farnesyl-L-cysteine), aromatic aldehydes with anti-inflammatory properties (e.g., 4-ethoxy benzaldehyde), etc., as well as any compatible combinations thereof); chemicals or botanical extracts with antihistamine properties; chemicals or botanical extracts with anti-microbial properties (e.g., antibiotics including, but not limited to gentamicin, penicillins, cephalosporins, quinolones, ciprofloxacin, and/or novobiocin); chemicals or botanical extracts with anti-fungal properties (e.g., ketoconazole, naftifine hydrochloride, oxiconazole nitrate, sulconazole nitrate, urea, terbinafine hydrochloride, selenium sulfide, etc.); chemicals or botanical extracts with anti-mite properties (e.g., crotamiton, ivermectin, permethrin, etc.); chemicals or botanical extracts with anti-acne properties (i.e., benzoyl peroxide, salicylic acid, retinoic acid, tretinoin; alpha-hydroxy acids; antibiotics, etc.); chemicals or botanical extracts with anti-parasitic properties; chemicals or botanical extracts with anti-dandruff properties; chemicals or botanical extracts with anti-seborrheic properties; keratolytic agents or botanical extracts with keratolytic properties (i.e., alpha-hydroxy acids; beta-hydroxy acids, poly-hydroxy acids, urea, salicylic acid, etc.); chemicals or botanical extracts with anti-androgen properties; chemicals with astringent properties; serine protease inhibitors; saturated dicarboxylic acids; alpha hydroxy acids (e.g., glycolic acids, lactic acid, malic acid, citric acid, tartaric acid, etc.); beta hydroxy acids (e.g., carnitine, 3-hydroxybutyric acid, 3-hydroxypropionic acid, β-hydroxy β-methylbutyric acid, salicylic acid, etc.).

Other compounds or active ingredients can include retinoic acid, tretinoin, isotretinoin, adapalene, retinol, and/or derivatives; benzoyl peroxide; dapsone; kinetin ($N^6$-furfuryladenine) and derivatives (e.g., furfurylaminotetrahydropyranyladenine); niacinamide (nicotinamide); sunscreens; antioxidants; emollients; humectants; skin moisturizers; skin protectants; skin barrier enhancers; skin penetration enhancers; minerals suitable for cosmetic use (e.g., talc, mica, iron oxides, etc.); make-up suitable for cosmetic use; peptides, fatty acid peptides, or combinations thereof; color additives suitable for cosmetic use; optical blurring agents suitable for cosmetic use; peptides and/or fatty acid peptides; phospholipids (e.g., phosphatidylcholines, lysophosphatidylcholines, lecithins, lysolecithin, etc.); growth factors and/or cytokines (e.g., TGF-betas, EGF, PDGF, IL-10, etc.), cell lysates (e.g., dermal fibroblast cell lysate, stem cell lysate, processed skin cell proteins (PSP®), etc.), conditioned cell culture mediums (e.g., conditioned cell culture medium from dermal fibroblasts, conditioned cell culture medium from stem cells, Nouricel-MD®, etc.); cell lysates or cell extracts, stem cell lysates or extracts, components from stem cells, and/or conditioned cell culture medium; ingredients stimulating epidermal or other human stem cells; skin conditioning agents; skin lightening and/or brightening agents; anti-wrinkle and/or anti-aging agents; plant and/or vegetable extracts (e.g., extracts and/or concentrates such as lyophilisates, evaporates, distillates, filtrates, etc.) from yeast, brewer spent grain (byproduct of beer brewing), barley, soybean, soybean milk, oat, lavender, licorice, ginger, ginseng, turmeric, apple, sea whip, algae, aloe vera (barbadensis) leaves, cactus, tea, chamomile, birch tree, etc.; vegetable oils; silicon oils; fatty acid and/or fatty acid esters; as well as any mixtures thereof. Exemplary fatty acid and/or fatty acid esters include, but are not limited to, linoleic acid, linolenic acid and/or esters thereof.

By way of non-limiting example, the additional compounds or active ingredients may further contain extracts (e.g., extracts and/or concentrates such as lyophilisates, evaporates, distillates, filtrates, supercritical fluid (e.g., carbon dioxide) extracts, etc.) from fish cartilage, shark cartilage, or marine invertebrates such as sea cucumber or sea urchin.

Any of the methods of the invention may also involve the administration of and any of the compositions for use of the invention may further contain one and more of metronidazole, sulfacetamide, sodium sulfacetamide, sulfur, tetracylines, doxycycline, clindamycin, clindamycin phosphate, erythromycin, and/or minocycline. In some embodiments, any of the methods of the invention may also involve the administration of and any of the compositions for use may further contain azelaic acid. In some embodiments, any of the methods of the invention may also involve the administration of and any of the compositions for use may further contain calcium dobesilate. In still further embodiments, any of the methods of the invention may also involve the administration of and any of the compositions for use may further contain caffeine, theobromine, theophylline and/or a derivative thereof (i.e., xanthines). Additionally, any of the methods of the invention may also involve the administration of and any of the compositions for use may further contain vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E and vitamin K, creatine, carnitine, and essential fatty acids such as linoleic acid and/or linolenic acid.

In other embodiments, any of the methods of the invention may also involve the administration of and any of the compositions for use may further contain zinc salts such as, for example, zinc sulfate, zinc chloride, zinc glycinate, zinc gluconate, zinc-histidine, zinc L-2-pyrrolidone-5-carboxylate (zinc PCA), zinc salt of linoleic acid, zinc salt of linolenic acid, zinc salt of azelaic acid, zinc peptides, zinc oxide, or combinations thereof.

Moreover, any of the methods of the invention may also involve the administration of and any of the compositions for use may further contain copper salts including, but not limited to, copper sulfate, copper chloride, copper glycinate, copper gluconate, copper-histidine, copper L-2-pyrrolidone-5-carboxylate (copper PCA), copper salt of linoleic acid, copper salt of linolenic acid, copper salt of azelaic acid, copper peptides, or combinations thereof.

Any of the compositions described herein can be administered to any patient suffering from a skin condition or disorder in order to treat the condition. For example, the composition can be administered to a patient or subject suffering from a disorder selected from rosacea, psoriasis, acne, seborrheic dermatitis, atopic dermatitis, skin cancers such as melanoma, skin wounds and ulcers, and/or other skin disorders associated with deregulation of the skin's antimicrobial peptide formation and/or processing.

In any of the methods described herein, the compositions of the invention can administered to the subject in an amount (i.e., strength or concentration of said antimicrobial peptide sequestering compound in said composition); administered dose (i.e., quantity of said composition applied topically per skin surface (e.g., administered dose onto the surface of the skin of 0.2 to 2 mg of the composition per $cm^2$); frequency of administration (i.e., daily, twice daily, three times daily, once weekly, twice weekly, etc.) and over a duration of treatment (i.e., for at least one to two weeks) that is suitable for the subject affected by the skin disorder or disease and is sufficient to cause a decrease in one or more symptoms associated with the skin disorder and disease.

Those skilled in the art will recognize that the symptoms associated with rosacea may include a tendency to flush or blush easily; a increased number of spider-like blood vessels (telangiectasia) of the face; chronic skin redness or erythema; acne-like skin eruptions, including, but not limited to, pustular and/or papular lesions; a burning or stinging sensation of the face; a red and bulbous nose; and/or any combination thereof.

Those skilled in the art will recognize that the symptoms associated with acne (also called acne vulgaris or cystic acne) may include acne lesions or eruptions, cysts, pustules, blackheads and whiteheads; but also crusting of skin eruptions, inflammation and redness around skin eruptions, as well as scarring of the skin related to those lesions and eruptions.

Those skilled in the art will recognize that the symptoms associated with atopic dermatitis (also called eczema) may include itching, dryness or leathery skin areas, skin redness or inflammation, rash, blisters with oozing and crusting, as well as raw areas of the skin from scratching.

Those skilled in the art will recognize that the symptoms associated with psoriasis may include irritated patches of skin, redness (often seen on the elbows, knees, and trunk, but can appear anywhere on the body) and flaky patches on the scalp. The patches (or dots) may be pink-red in color (like the color of salmon), dry and covered with silver, flaky skin (scales), and/or raised and thick.

Also provided herein are compositions for treating skin diseases or disorders associated with deregulation of the skin's antimicrobial peptide formation, processing or both, wherein the composition is prepared from: a) a first phase containing about 60.30% (by weight) water, about 0.1% disodium EDTA, about 0.25% (by weight) xantham gum, about 1.25% (by weight) ammonium acryloyldimethyltaurate/beheneth-25 methacrylate crosspolymer, and about 1.5% (by weight) hydroxypropyl starch phosphate; b) a second phase containing about 14% (by weight) water, about 1.5% (by weight) caffeine; about 0.1% (by weight) dextran sodium sulfate, about 1% (by weight) zinc PCA, about 15% (by weight) glycerin), and about 1% (by weight) phenoxyethanol; c) a third phase containing about 1% (by weight) hydroxylpropyl starch phosphate; and d) a fourth phase containing about 3% caprylyl methicone, wherein the combined weight of all phases is 100% (by weight).

In another aspect, the invention also provides compositions for treating skin diseases or disorders associated with deregulation of the skin's antimicrobial peptide formation, processing or both, wherein the composition is prepared from: a) a first phase containing about 60.30% (by weight) water, about 0.1% disodium EDTA, about 0.25% (by weight) xantham gum, about 1.25% (by weight) ammonium acryloyldimethyltaurate/beheneth-25 methacrylate crosspolymer, and about 1.5% (by weight) hydroxypropyl starch phosphate; b) a second phase containing about 13.85% (by weight) water, about 1.5% (by weight) caffeine; about 0.25% (by weight) dextran sodium sulfate, about 1% (by weight) zinc PCA, about 15% (by weight) glycerin), and about 1% (by weight) phenoxyethanol; c) a third phase containing about 1% (by weight) hydroxylpropyl starch phosphate; and d) a fourth phase containing about 3% caprylyl methicone, wherein the combined weight of all phases is 100% (by weight).

In still a further aspect, the invention provides compositions for treating skin diseases or disorders associated with deregulation of the skin's antimicrobial peptide formation, processing or both, wherein the composition is prepared from: a) a first phase containing about 60.04% (by weight) water, about 0.1% disodium EDTA, about 0.25% (by weight) xantham gum, about 1% (by weight) hydroxypropyl starch phosphate, and about 1% (by weight) hydroxyethyl acrylate/sodium acryloyldimethyl taurate copolymer and isohexadecane and polysorbate-60; b) a second phase containing about 15% (by weight) water, about 1.5% (by weight) caffeine; about 0.5% (by weight) dextran sodium sulfate, about 1% (by weight) zinc PCA, about 0.2% (by weight) chlorphenesin, about 15% (by weight) glycerin), and about 0.5% (by weight) phenoxyethanol; c) a third phase comprising about 1.5% (by weight) hydroxylpropyl starch phosphate and about 0.41% (by weight) hydroxyethyl acrylate/sodium acryloyldimethyl taurate copolymer and isohexadecane and polysorbate-60; and d) a fourth phase comprising about 2% caprylyl methicone, wherein the combined weight of all phases is 100% (by weight).

In various embodiments, the invention also provides pharmaceutical formulation containing any of the compositions disclosed herein and at least one pharmaceutically acceptable carrier. Similarly, the invention also provides cosmetic formulations containing any of the compositions disclosed herein and at least one cosmetically acceptable carrier.

The invention also provides kits containing, in one or more containers, the pharmaceutical and/or cosmetic formulations described herein. Those skilled in the art will recognize that these kits may additional contain instructions for use of the pharmaceutical and/or cosmetic formulations in the treatment of skin diseases or disorders associated with deregulation of the skin's antimicrobial peptide formation, processing or both. Finally, the invention provides unit dosage forms of the pharmaceutically and/or cosmetically effective amount of the compositions described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description.

DETAILED DESCRIPTION

In the specification and the appended claims, the singular forms include plural references unless the context clearly dictates otherwise. For convenience, certain terms used in the specification, examples and claims are collected here.

Before the present compositions and methods are described, it is to be understood that this invention is not limited to the particular compositions, processes, or methodologies described herein, as these may vary. It is also understood that the terminology used in the description is for the purpose of describing the particular versions or embodiments only, and is not intended to limit the scope of the present invention, which will be limited only by the appended claims.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. Any formulas provided herein are shown without a definitive stereochemistry at certain positions. The present invention includes all stereoisomers of such formulas and acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration.

Those skilled in the art will recognize that it has recently been demonstrated that dysfunction (or deregulation) in skin's production and processing of antimicrobial peptides plays a key role in pathogenesis of several cutaneous diseases. Cutaneous production of antimicrobial peptides is a primary system for protection from microbial invasion. Antimicrobial peptides are important effector molecules of the innate immune defense protecting epithelial barriers. To date, more than seven hundred antimicrobial peptides have been isolated from diverse species such as plants, amphibians, insects and mammals.

All antimicrobial peptides are synthesized as proforms, which are subsequently processed into mature peptides of various lengths. Despite diverse structural motifs, a common feature of most of these peptides is that they are cationic and form amphipathic structures. Antimicrobial peptides show a broad spectrum of antimicrobial activity against a wide range of pathogens including bacteria, fungi, enveloped viruses and protozoa and therefore play an important role in the innate host defense. The mode of action of most antimicrobial peptides is incompletely understood. Many antimicrobial peptides increase the permeability of the bacterial cytoplasmic membrane as part of their killing mechanism. Apart from being natural antibiotics, recent evidence suggests that antimicrobial peptides additionally play a crucial role as signaling molecules in linking innate and adaptive immune responses. Antimicrobial peptides can mediate chemotaxis of dendritic cells and T cells and maturation and activation of dendritic cells and by this means activate the acquired immune responses against infectious agents.

In human skin, keratinocytes are a major source of antimicrobial active peptides. In addition, cells present in skin like neutrophils, mast cells, T cells, eccrine sweat glands, hair bulb cells and sebocytes are also able to produce antimicrobial peptides. They can be expressed constitutively or after an inflammatory stimulus.

In skin, various families of antimicrobial peptides have been identified, including but not limited to cathelicidins, defensins and dermcidins. RNase 7, psoriasin (S100A7), and adrenomedullin are other antimicrobial peptides described in skin (see Infectious Disorders—Drug Targets 2008, 8, 135-143).

The cathelicidin family is characterized by a conserved N-terminal cathelin domain and a variable C-terminal antimicrobial domain that can be released from the precursor protein after cleavage by proteinases. LL-37 is the C-terminal part of the only human cathelicidin identified to date called human cationic antimicrobial protein (hCAP18), which is mainly expressed by neutrophils, mast cells and keratinocytes after an inflammatory stimulus or in inflammatory skin disorders. The cathelicidin hCAP18/LL-37 is a multifunctional molecule that may mediate various host responses, including bactericidal action, chemotaxis, epithelial cell activation, angiogenesis, epithelial wound repair and activation of chemokine secretion. Mature LL-37 peptide as well as several antimicrobial active truncated forms of the precursor protein are found in sweat, however only at very low amounts. LL-37 has a broad spectrum of antimicrobial activity against gram positive and gram-negative bacteria. Furthermore, it shows synergistic effects with other antimicrobial peptides such as the β-defensins.

Defensins are cationic peptides with a molecular weight of 3-5 kDa and are divided into alpha, beta and theta subfamilies based on the position of the intra-molecular disulfide bridges. In humans only the α- and β-defensins are expressed. Defensins exhibit antimicrobial activity against bacteria, fungi and enveloped viruses and have been isolated from neutrophil granules, macrophages and epithelial cells. Whereas in human skin the α-defensins are expressed in neutrophils, keratinocytes in human skin express the β-defensins 1, 2, 3 and 4. Human β-defensin-1 is constitutively produced in the suprabasal layers of the epidermis at low amounts. Human β-defensin-1 and -2 expression is increased by injury or inflammation of the skin like in lesional skin of psoriatic scales and is induced by pro-inflammatory cytokines and bacterial contact. Human β-defensin-2 is localized to the upper malphigian layer of the epidermis and the stratum corneum, where it is stored in lamellar bodies of stimulated keratinocytes of the spinous layer of the epidermis. Human β-defensin-1 and -2 exhibit antimicrobial activity mainly against gram-negative bacteria, whereas human β-defensin-3 shows a broad spectrum of antimicrobial activity against gram positive and gram-negative bacteria including multi-resistant bacteria.

Dermcidin is an antimicrobial peptide with activity against gram-positive and gram-negative bacteria and C. albicans. Dermcidin expression is restricted to human skin where it is constitutively expressed in eccrine sweat glands, secreted into sweat and transported to the epidermal surface. In sweat several proteolytically processed, N-terminal truncated dermcidin-derived antimicrobial peptides like dermcidin-1L (48 mer, anionic), dermcidin-1 (47 mer, anionic) and SSL-25 (25 mer, cationic) are found differing in charge and length. Dermcidin-derived peptides contribute to the first line of defense by building a constant barrier that overlies the epithelial skin. Dermcidin-1 shows antimicrobial activity against pathogenic microorganisms such as S. aureus, E. coli, E. faecalis and C. albicans under in vitro conditions resembling human sweat.

In individuals with rosacea, an abnormally high level of cathelicidin is found in their facial skin. In addition, the proteolytically processed forms of cathelicidin peptides are increased and/or different in rosacea skin as compared to skin from normal individuals. These cathelicidin peptides are a result of a post-translational processing abnormality that is associated with an increase in proteases (i.e., stratum corneum tryptic enzyme) in the epidermis.

Alterations of antimicrobial peptide expression has also been observed in other skin disorders and diseases than rosacea. (See Infect Disord Drug Targets 8: 135-43 (2008) (incorporated herein by reference)).

As in rosacea, overexpression of antimicrobial peptides can lead to increased protection against skin infections as seen in patients with psoriasis, inflammatory skin-diseases which rarely result in superinfection. In psoriasis, antimicrobial peptides including LL37, human beta defensins 2 and 3 are all upregulated and are believed to contribute to the inflammation and the pathogenesis of the disease (see Curr Pharm Des 16: 1024-39 (2010) (incorporated herein by reference)). In psoriasis cathelicidin peptide converts self-DNA to a potent stimulus in an autoinflammatory cascade (see J Allergy Clin Immunol 122: 261-66 (2008) (incorporated herein by reference)). In other skin diseases, e.g. in patients with acne vulgaris, increased levels of antimicrobial peptides are often found in inflamed or infected skin areas indicating a role of these peptides in the protection from infection (Infect Disord Drug Targets 8: 135-43 (2008) (incorporated herein by reference)).

The expression of antimicrobial peptides in atopic dermatitis (eczema) is still emerging. Similarly as in psoriasis, it is speculated that a disturbed skin barrier may trigger antimicrobial peptides induction in atopic dermatitis (see J Invest Dermatol 130: 1355-64 (2010) (incorporated herein by reference)). However, another study indicated that skin lesions of patients with atopic dermatitis have a diminished expression of the beta-defensins and the cathelicidin LL-37. (See Semin Cutan Med Surg, 27:144-50 (2008) (incorporated herein by reference)). Furthermore, these patients were shown to have a reduced amount of dermcidin in their sweat which correlates with an impaired innate defense of human skin in vivo.

In addition, decreased levels of antimicrobial peptides are associated with burns and chronic wounds.

Accordingly, provided herein are compositions and methods useful for the treatment of diseases and disorders of the skin including, but not limited to, rosacea, psoriasis, acne, atopic dermatitis, skin cancers such as melanoma, skin wounds and ulcers, and/or other skin disorders associated with deregulation of the skin's antimicrobial peptide formation and/or processing. Such compositions include one or more antimicrobial peptide sequestering compounds. The use of such compounds provides an effective treatment of skin disorders and diseases with dysfunction in production and processing of antimicrobial peptides.

Preferably, the antimicrobial peptide sequestering compound does not target and inhibit antimicrobial peptide (i.e., cathelicidin) proteolysis and/or result in a reduction in antimicrobial peptide (i.e., cathelicidin) production or activity, as described in published US Patent Application 20090318534 (incorporated herein by reference). Rather, that application discloses a treatment of rosacea by inhibiting cathelicidin expression through topical inhibition of Vitamin D or the Vitamin D receptor (using a vitamin D inhibitor or a vitamin D receptor antagonist) to reduce up-regulation of cathelicidin. US20090318534 further discloses a treatment of rosacea by inhibiting the kallikrein stratum corneum tryptic enzyme (SCTE), an enzyme that cleaves the cathelicidin precursor protein, using serine protease inhibitors (such as aprotinin and 4-(2-aminoethyl)-benzenesulfonylfluoride (AEBSF)) and also provides methods for the treatment of inflammatory diseases and disorders (including rosacea and/or acne) by inhibiting or reducing cathelicidin expression or activity using antibodies and small molecule agents as well as antisense, ribozyme, and/or gene therapy techniques.

Such treatment methods may include treatment at the site of inflammation through topical inhibition of Vitamin D activity, inhibition of a Vitamin D receptor activity, or use of an inhibitor of a protease that cleaves full length cathelicidin into its active fragments. Moreover, US Patent Application 20090318534 further discloses that an inflammatory inhibitory composition (e.g., a rosacea inhibitory composition) used in the treatment of rosacea can include (i) a cathelicidin activity or expression inhibitor (i.e., any agent that reduces the biological activity of a cathelicidin polypeptide including, for example, an N-terminal or C-terminal domain (e.g., LL37) of cathelicidin, (ii) a serine protease activity or expression inhibitor (i.e., any agent that reduces the biological activity of a serine protease polypeptide such as a SCTE inhibitor, or (iii) a combination of (i) and (ii).

Exemplary cathelicidin inhibitory agents include antibodies that bind to and inhibit a cathelicidin polypeptide or functional fragment thereof, enzymes that degrade cathelicidin polypeptide to inactive peptides and the like. Cathelicidin expression inhibitors can include, for example, antisense molecules, ribozymes and small molecule agents (e.g., vitamin D3 antagonists) that reduce the transcription or translation of a cathelicidin polynucleotide (e.g., DNA or RNA). Exemplary serine protease inhibitory agents include antibodies that bind to and inhibit a serine protease polypeptide or functional fragment thereof, enzymes that degrade a serine protease polypeptide to inactive peptides, and the like. A serine protease expression inhibitor includes, for example, antisense molecules, ribozymes and small molecule agents (e.g., vitamin D antagonists) that reduce the transcription or translation of a serine protease polynucleotide (e.g., DNA or RNA).

However, US Patent Application 20090318534 does not disclose the use of antimicrobial peptide sequestering compounds, which are used in the compositions of the instant invention for the treatment of diseases and disorders of the skin including, but not limited to, rosacea, acne, psoriasis, atopic dermatitis, skin cancers such as melanoma, skin wounds and ulcers, and/or other skin disorders associated with deregulation of the skin's antimicrobial peptide formation and/or processing.

Specifically, as used herein, "antimicrobial peptide sequestering compounds" are defined as chemical compounds other than a peptide, polypeptide or protein (i.e., poly-amino acids) which have the capacity to bind an antimicrobial peptide by attractive intermolecular forces (i.e., Coulomb forces, Van der Waals forces, etc.). More specifically, by binding to the antimicrobial peptide such as a cathelicidin, the antimicrobial peptide sequestering compounds are able to alter the antimicrobial peptide's capacity to diffuse (e.g., in water, in biological fluids, in skin, in sebum, in artificial matrix such as polyacrylamide gel, agarose gel, etc.), its capacity to be absorbed (e.g., from the skin surface into deeper layers of the skin tissue including epidermis and dermis), or its capacity to be adsorbed (e.g., adherence to the skin surface, and/or adherence to surface or interface of other biological tissues). Furthermore, the interaction between the antimicrobial peptide sequestering compound and the antimicrobial peptide can be reversed by certain chemicals (e.g., salts, cations, polycations), which are able to interfere with, disrupt, and/or weaken the attractive intermolecular forces between the antimicrobial peptide sequestering compound and the antimicrobial peptide.

The use of an antimicrobial peptide sequestering compound for the treatment of rosacea and other skin disorders and diseases associated with dysfunction in the skin's production and processing of antimicrobial peptides in accordance with the instant invention is not predictable based on the teachings of the prior art. Rather, the antimicrobial peptide sequestering compounds described herein manifest their efficacy solely by binding the antimicrobial peptide through non-specific intermolecular forces, which are different and less specific than the interactions between two (or more than two) poly-amino acid complexes (i.e., peptides, polypeptides, proteins) which form an antigen-antibody complex.

In contrast, the unique part of the antigen recognized by an antibody is called the epitope. Epitopes bind with their antibody in a highly specific interaction, which allows antibodies to identify and bind only their unique antigen. Accordingly, those skilled in the art will easily recognize that the complex formed by antibody-antigen interaction as disclosed in US Patent Application 20090318534 is different from an antimicrobial peptide that is sequestered by an antimicrobial peptide sequestering compound other than a poly-amino acid (i.e., peptide, polypeptide, protein), as disclosed in the present invention.

Moreover, as disclosed herein, the antimicrobial peptide sequestering compounds also do not inhibit the formation (i.e., through inhibition of gene expression and/or transcription or translation of antimicrobial peptide polynucleotide) or the biological activity (i.e., through use of antibodies that bind to and inhibit the antimicrobial peptide or functional fragment thereof) of the antimicrobial peptide. Likewise, they also do not inhibit the degradation of antimicrobial peptide (i.e., through inhibition of enzymes that degrade the antimicrobial peptide to inactive peptides and like) and do not enhance its protection (i.e., through protection or enhancement of enzymes that protect the antimicrobial peptide from its degradation to inactive peptides and the like) from degradation.

In addition, the efficacy of the antimicrobial peptide sequestering compounds in the treatment of rosacea and other skin disorders and diseases associated with dysfunction in the skin's production and processing of antimicrobial peptides is surprising and unexpected in view of the teachings of the prior art for a number of reasons. First, the sequestering of the antimicrobial peptide by the antimicrobial peptide sequestering compound is a complex and unpredictable process which strongly depends on a number of factors including the environment (i.e., presence of biomolecules such as ions, salts, lipids, amino acids, proteins, extracellular matrix components, sugar, DNA, etc., which are naturally present in the skin and/or on the skin surface; the water content (hydration) of skin; and/or the amount of sebum (e.g., oiliness) present on the skin surface) and the location where (i.e., in the skin (dermis, epidermis, appendages) tissue including the skin surface) the interaction between the antimicrobial peptide sequestering compound and the antimicrobial peptide takes place. Second, the sequestering of the antimicrobial peptide by the antimicrobial peptide sequestering compound either does not result in a reduced content (i.e., concentration) of the antimicrobial peptide in the skin or on the skin surface, or it only affects its concentration minimally (for instance related to the dilution of the anti-microbial peptide after application of said compound or composition to skin) in the skin or on the skin surface, since the sequestering of the antimicrobial peptide does not affect (i.e., inhibit) the natural formation of the antimicrobial peptide in human skin. Third, the sequestering of the antimicrobial peptide by the antimicrobial peptide sequestering compound is reversible (e.g., in the presence of an elevated concentration of cations), which means that the binding of the antimicrobial peptide by the antimicrobial peptide sequestering compound may be weakened or eliminated, thereby resulting in the release of the antimicrobial peptide, which is once again able to cause and aggravate the skin disease and disorder.

The compositions and methods of the instant invention also provide some significant advantages as compared to prior art compositions and methods (see, e.g., US Patent Application 20090318534). For example, the use of antibodies (i.e., immunoglobulins) or antibody mimetic peptides or proteins that specifically bind to an antimicrobial peptide (e.g., an anti-cathelicidin antibody, anti-LL-37 antibody, or an anti-defensin antibody) are not suitable for topical administration for different reasons. Most importantly, antibodies are generally unstable and undergo spontaneous hydrolysis, oxidation, and/or conformational changes (denaturation), which can result in loss or reduction of their binding activity (i.e., the highly specific interaction between the antibody and the antigen is altered and is therefore weaker or impossible). In addition, because of their large molecular size (i.e., molecular weight (expressed in grams per mol) or molecular volume), antibodies do not penetrate the skin in amounts sufficient to manifest a biological activity in the skin tissue. As a consequence, an antibody (or antibody mimic peptides or proteins) of an antimicrobial peptide (as disclosed in US Patent Application 20090318534) is not suited for topical use.

Additionally, those skilled in the art will recognize that proteins made for cosmetic or pharmaceutical uses, such as, for example, the antibodies or antibody mimetic peptides or proteins that specifically bind to an antimicrobial peptide disclosed in US Patent Application 20090318534, can induce a variety of adverse effects in humans. For example, immunotoxic effects deserve particular attention (see Expert Opin Drug Metab Toxicol 4:1537-49 (2008) (incorporated herein by reference)).

Because of their structure and origin, proteins made for cosmetic or pharmaceutical uses are intrinsically immunogenic. Despite extensive laboratory and clinical studies that were instrumental in delineating general concepts about key factors involved in immunogenicity, it is now impossible to anticipate to what extent such a protein is immunogenic in humans. Specific antibodies are frequently detected in the sera of treated patients, and while they are often inconsequential, they can also be neutralizing and result in decreased efficacy. In addition, anaphylactic reactions induced by such proteins have been rarely reported and as has true serum sickness. Therefore, the immunotoxic effects of proteins made for cosmetic or pharmaceutical uses are frequent, sometimes severe and may even be potentially life-threatening.

In contrast, in the compositions of the instant invention, the antimicrobial peptide sequestering compound is not a peptide, polypeptide or protein and the antimicrobial peptide sequestering compound is therefore not susceptible to instabilities and immunotoxic effects typical for peptides, polypeptides, and proteins, such as those disclosed in US Patent Application 20090218534. In addition, the antimicrobial peptide sequestering compound is generally of a smaller molecular size than an antibody (which is typically more than 100,000 grams per mol). Preferably, the antimicrobial peptide sequestering compound is between 100 to 100,000 grams per mol; more preferably between 100 to 25,000 grams per mol, and most preferably between 100 to 10,000 grams per mol. Thus, these compounds are able to penetrate the skin in a more efficient manner than an antibody (or antibody mimic peptides or proteins) of an antimicrobial peptide (for example, as disclosed in US Patent Application 20090318534).

In addition, the antimicrobial peptide sequestering compound of this invention is neither a vitamin D3 antagonist or a serine protease inhibitor. Because vitamin D3 and serine protease inhibitors including kallikrein SCTE are essential for the regulation of many functions in skin and other organs (e.g. bones) that are unrelated to antimicrobial peptides, interfering with essential biological pathways of vitamin D and serine protease may result in undesired side effects when using a vitamin D3 antagonist and/or a serine protease inhibitor over a prolonged period of time (e.g., two and more weeks).

In one aspect of the invention, the antimicrobial peptide sequestering compound reduces the availability of the antimicrobial peptide (i.e., cathelicidin) in the skin and on the surface of the skin, wherein the reduction in the availability of the antimicrobial peptide can be understood as a reduced presence of "free" antimicrobial peptides in the skin or on the skin surface. Only "free" antimicrobial peptides are able to cause the biological signal (response) characteristic of antimicrobial peptides, which ultimately leads to said skin disorder/disease (e.g., rosacea). For the present invention, an antimicrobial peptide, which is sequestered by said antimicrobial peptide sequestering compound is defined as not "free", and, therefore, is not available to cause the biological signal characteristic of antimicrobial peptides. Moreover, as noted, this reduction is not achieved through (i) inhibition of cathelicidin activity or expression, (ii) inhibition of serine protease activity or expression, (iii) inhibition of transcription or translation of cathelicidin polynucleotide, (iv) inhibition of expression of cathelicidin polypeptide (v) degradation of cathelicidin polypeptide to inactive peptides, (vi) Vitamin D3 antagonist activities or as vitamin D receptor inhibitor, or (vii) any combination thereof.

Rather, the sequestration of an antimicrobial peptide by the antimicrobial peptide sequestering compound (i) limits the mobility of the antimicrobial peptide (i.e., diffusion and/or transport), (ii) reduces the accessibility for converting the antimicrobial peptide (i.e., by serine proteases), (iii) decreases the permeability of the antimicrobial peptide (i.e., through skin, through cell wall into cell cytoplasm, within extracellular space of skin, etc.), (iv) limits the ability of the antimicrobial peptide to bind to its receptor or other ligand-receptor interactions characteristic for the antimicrobial peptide, or (v) any combination thereof. In addition, the sequestration of an antimicrobial peptide by said anti-microbial peptide sequestering compound is the result of non-specific physical interactions (i.e., electrostatic forces, Van der Waals forces) between the antimicrobial peptide (e.g., cathelicidin) and the antimicrobial peptide sequestering compound.

Importantly, the compositions of the invention should be mild and substantially non-irritating. The present invention provides stable and well tolerated (i.e., composition causes no or only low and acceptable skin irritation, or skin discomforts such as stinging, burning and itching after topical application to skin such as face) compositions for topical application to the skin to treat rosacea, psoriasis and other skin diseases and disorders associated with dysfunction of antimicrobial peptide expression in humans.

Stable compositions can be obtained by (1) selecting appropriate concentration(s) for the antimicrobial peptide sequestering compound agent, (2) selecting appropriate type(s) of formulation (e.g., a liquid, a foam, a mousse, a spray, an aerosol, an oil-in-water emulsion, a water-in-oil emulsion, a triple emulsion, a nanoemulsion, a microemulsion, a hydrogel, a solution, a paste, a jelly, a patch, a wipe, a cloth, and/or a dispersion or suspension) for the composition, (3) selecting appropriate ingredient(s) that keep the antimicrobial peptide sequestering compound and the composition stable, (4) selecting appropriate container(s) for the composition suitable for topical administration (e.g., tube, airless pump, jar, vial, monodose, etc.), and/or (5) selecting appropriate condition(s) allowing the preparation of the composition (e.g., preparation of composition by suitable homogenizers for preparation of semi-solid formulations, preparation of composition within appropriate temperatures ranges where the antimicrobial peptide sequestering compound and the other ingredients remain chemically stable, preparation of composition under inert gas, etc.).

The term "stable" or the stability of the composition includes physical stability (e.g., viscosity, odor, appearance, texture, etc.) and may also include the chemical stability of the antimicrobial peptide sequestering compound as well as selected other ingredients of the composition (i.e., a drug active (e.g., metronidazole)). Chemical stability can be assessed using HPLC or other appropriate analytical methods. When the composition is placed (e.g., filled) into a suitable container (e.g., tube, pump, jar, etc.), the drug active in the composition should be chemically stable (i.e., less than a ±10% change in the content as compared to the baseline value) for at least six months under normal storage condition (i.e., room temperature; or common temperature fluctuations occurring in house/living room/bath room). Stability may also be tested under accelerated conditions at elevated temperatures (e.g., 40° C. or higher) in order to predict the stability of the composition under normal storage condition.

The term "stable" when applied to the compositions of the instant invention may further be defined as no or only minor color changes when the composition is placed on a flat and inert surface (i.e., removed from its container) under normal ambient air and light conditions (i.e., air and light conditions as normally exist in the living room at home) for at least one month at room temperature (about 25° C.).

In contrast to prior art compositions, the active compound(s) in the compositions disclosed herein are antimicrobial peptide sequestering compounds. Preferably this compound is an anionic chemical of molecular weight of at least 100 grams per mol. In various embodiments, the anionic chemical may comprise ions of alkali metals, alkaline earth metals, or transition metals (e.g., Na, K, Ca, Mg, Ba, Zn, Cu, Zr, Ti, Bi, or Mn); or ammonium ion ($NH_4^+$), quarternary ammonium cations, and/or the protonated forms of carbohydrates or derivatives of carbohydrates with an amine group (e.g., amino acid, methylamine, dimethylamine, trimethylamine, 2-aminopentane, etc.) as counter ions.

The anionic chemical may be an anionic polymer of a molecular weight of up 100,000 grams per mol other than a poly-amino acid (i.e., peptide, polypeptide, protein). In one preferred embodiment, the compound is a sulfated or polysulfated monosaccharide, a sulfated or polysulfated disaccharide, a sulfated or polysulfated polysaccharide (e.g., dextran sulfate, chondroitin sulfate), and/or salts and complexes thereof. Other preferred sulfated saccharides include, but are not limited to, pentosan polysulfate, sucrose sulfate, sucrose octasulphate, fucoidan, sulfated galactan, heparan sulfate, sulfated glucan, starch sulfate, cellulose sulfate, sulfated glycosaminoglycans, and/or salts and complexes thereof. The preferred anionic chemical for use in the compositions of the claimed invention does not encompass aluminum salts and complexes.

Other compounds suitable for use in the methods and compositions disclosed herein include, but are not limited to carrageenans (*Chondrus Crispus*), algae extracts, aloe vera extracts, cactus extracts, shark, or fish cartilage extracts, plant extracts rich in sulfated saccharides (mono-, di-, poly-), as well as salts and complexes thereof.

Suitable compounds may be obtained by preparing sulfated or polysulfated polymers by chemical synthesis. Such synthetic compounds that can be obtained by chemical synthesis may include, but are not limited to, sulfated or polysulfated polysaccharides. Sulfated or polysulfated polymers may be obtained by sulfation (also spelled sulphation) of a polymer including but not limited to polysaccharides and polyglycols. Sulfation can be achieved by several methods by which esters or salts of sulfuric acid (sulfates) are formed. The esters are commonly prepared by treating an alcohol group with sulfuric acid, sulfur trioxide, chlorosulfuric acid, or sulfamic acid.

In some embodiments, the polysulfated polymer may be a polymeric sulfonic acid, poly(vinyl sulfate), or poly(anethole sulfonate). As an example, 'Aristofiex® HMP' (by Clariant) is a polymeric sulfonic acid.

Furthermore, the antimicrobial peptide sequestering compound may be also a phosphate or polyphosphate including, but not limited to, a monosaccharide phosphate, a disaccharide phosphate, and a polysaccharide phosphate. As an example, said antimicrobial peptide sequestering compound is a glycerophosphate salt. Other examples of suitable phosphates or polyphosphates include starch phosphate, hydroxypropyl starch phosphate (e.g., 'Structure XL' by National Starch, LCC). Phospholipids, phosphatidylcholines including lecithin (e.g. from soy bean) are additional examples representative of the antimicrobial peptide sequestering compounds suitable for use.

Likewise, the antimicrobial peptide sequestering compound include further carboxylates, polyhydroxy acids including, but not limited to, hyaluronic acid, polylactic acid, alginate, and/or salts and complexes thereof.

The antimicrobial peptide sequestering compounds used in accordance with the instant invention may also include compounds which further bind or sequester the heparin binding growth factors and cytokines (i.e., fibroblast growth factors, vascular endothelial growth factors, and the like). For example, dextran sulfate is such a compound. Dextran sulfate can be of any origin, for example, dextran sulfate marketed by Pharmacia Biotech/Amersham Biosciences under the trademark Dextran Sulfate 10 sodium salt. For example, other suppliers of dextran sulfate are Sigma-Aldrich (i.e., Product Numbers D7037, D4911, D6924, D3257, D8787, D6001, and D8906; the dextran sulfate sodium salts are derived from *Leuconostoc mesenteroides*, strain B 512), MP Biomedicals (i.e., Catalog Number 101518) and Spectrum Chemical Manufacturing Corporation (i.e., Catalog Numbers DE131 or DE136).

In addition to the physicochemical properties of dextran sulfate, which are known to this art and which make it a good compound for cosmetic compositions (e.g., good solubility in water and saline solutions, high stability in solutions of pH ranging from 4 to 10 at room temperature), dextran sulfate also has properties of water absorption, a protective effect against the damage induced by free radicals, particularly in topical application, stabilization of proteins or unstable species and substances, and moisturization on account of its excellent hydrophilic properties. Biological properties of dextran sulfate such as an anti-coagulant effect, an inhibitory effect on enzymes such as hyaluronidase, glucosidases, elastase or even thrombin, and antiviral activity are also known.

With respect to the skin and skin protection, dextran sulfate is known for its anti-wrinkle, anti-inflammatory, anti-allergic and anti-aging properties as well as for its role in treating rough and flaky skin and in moisturization.

Escin (or aesin) is a chemical molecule consisting of glucuronic acid and two sugars (glucose-xylose) linked to an aglycone, deglucoescin which has a molecular weight of about 1131 grams per mol. This is a molecule which exists, for example, in plant extracts, particularly in extracts of common horse chestnut. In the prior art, escin is described in weight-reducing compositions, in compositions for promoting blood circulation, in compositions for treating the skin such as anti-inflammatory agents, for improving the cohesion between the dermis and the epidermis, and in skin-lightening cosmetic compositions. Escin has also been formulated into compositions for treating bags and wrinkles under the eyes.

U.S. Pat. No. 6,562,355 describes the use of a co-mixture of dextran sulfate and escin formulated into a physiologically acceptable medium for the treatment of redness/edema and/or sensitive skin. This co-mixture acts by inhibiting the vasodilation and/or exerting an anti-edema effect and/or soothing sensitive skin. In contrast, the compositions of the instant invention utilize antimicrobial peptide sequestering compounds that are topically applied in order to treat skin diseases and disorders such as rosacea.

The co-mixture described in U.S. Pat. No. 6,562,355 preferably comprises dextran sulfate, in the form of a sodium salt thereof. For example, the dextran sulfate has a molecular weight ranging from $2 \times 10^3$ to $5 \times 10^6$ and preferably from $5 \times 10^3$ to $10^5$. In contrast, in the compositions of the instant invention, the molecular weight of the dextran sulfate preferentially remains lower than $10^5$ grams per mol.

Preferably, the compositions described herein are suitable for topical administration (i.e., on top of skin surface, on top of mucosal surface, on top of finger nail or toe nail surface, onto hair). As used herein, topical administration includes, but is not limited to, cutaneous, scalp, hair, ocular, mucosal, buccal, vaginal, and/or vulvar administration.

The compositions of the invention incorporate the antimicrobial peptide sequestering compound at a concentration sufficient for demonstrating clinical efficacy in reducing one or more symptoms of rosacea and other skin disorders and diseases associated with dysfunction in skin's production and processing of antimicrobial peptides. For example, the compositions of the invention contain the antimicrobial peptide sequestering compound at a concentration between 0.01 w % to the limit of solubility of the antimicrobial peptide sequestering compound in the composition. Preferably, the amount of the antimicrobial peptide sequestering compound is between 0.05 w % and 25 w %. In some cases of plant or vegetable extracts (i.e., aloe, cactus, etc.), the amount of the antimicrobial peptide sequestering compound may be more then 25 w %.

These compositions are preferably in a formulation suitable for topical application (e.g., solution, suspension, gel, hydrogel, cream, emulsion, micro-emulsion, nano-emulsion, lotion, serum, spray, ointment, patch, tissue cloth, wipe, soap bar, mask, aerosol, paste, iontophoretic patch, skin delivery enhancing system or device, etc.). Other suitable formulations will be readily known to those skilled in the art.

The antimicrobial peptide sequestering compound is incorporated into the compositions to insure that the composition remains stable over a period of time reasonable for commercialization of a composition for topical administration (i.e., a shelf-life of between 6 to 36 months).

Any of the compositions disclosed herein may comprise additionally, for example, an anti-inflammatory agent including but not limited to corticosteroids (i.e., for short term use), non-steroidal anti-inflammatory drugs, anti-inflammatory interleukins (i.e. IL-1ra), anti-inflammatory fatty acids (i.e., linoleic acid, linolenic acid), aromatic aldehydes with anti-inflammatory properties (i.e., 4-ethoxy benzaldehyde); alpha hydroxy acids (i.e., glycolic acids, lactic acid, malic acid, citric acid, tartaric acid, etc.); beta hydroxy acids (i.e., carnitine, 3-hydroxybutyric acid, 3-hydroxypropionic acid, β-hydroxyl β-methylbutyric acid, salicylic acid, etc.); kinetin ($N^6$-furfuryladenine) and derivatives (i.e., furfurylaminotetrahydropyranyladenine), bisabolol, glycyrrhetinic acid, plant extracts with anti-inflammatory properties (i.e., tea extracts, chamomile extracts), isoprenylcystein analogues (i.e., N-acetyl-S-farnesyl-L-cysteine), niacinamide (nicotinamide); salts of 2,5-dihydroxybenzenesulfonate (e.g., calcium dobesilate); and/or a rosacea inhibitory agents including but not limited to one and more of metronidazole, sulfacetamide, sodium sulfacetamide, sulfur, dapsone, doxycycline, minocycline, clindamycin, clindamycin phosphate, erythromycin, tetracylines, and azelaic acid, and maleic acid.

Further, these compositions may also comprise one or more additional agents, compounds, and/or active or inactive ingredients. By way of non-limiting example, the compositions may also contain α-adrenergic receptor agonists including but not limited to α-adrenergic receptor agonists disclosed in WO 2009/065116, which is herein incorporated by reference in it entirety (e.g., clonidine, amphetamine, doxtroamphetamine, apraclonidine, dipivefrin, α-methyldopa, oxymetazoline, oxymetazoline hydrochloride, methoxamine, metaraminol, medetomidine, dexmedetomidine, ethylnorepinephrine, guanfacine, guanabenz, phenylephrine, phenylephrine hydrochloride, ephedrine, epinine, epinephrine, ethylnorepinephrine, levarterenol, lofexidine, norepinephrine, norphenylephrine, norephedrine, phenylpropanolamine, pemoline, propylhexadrine, pseudoephedrine, methamphetamine, α-methylnorepinephrine, methylphenidate, mephentermine, midodrine, mivazerol, moxonidine, desglymidodrine, tetrahydrozoline, tetrahydrozoline hydrochloride, cirazoline, amidephrine, brimonidine, brimonidine tartrate, naphazoline, isoproterenol, xylazine, xylometazoline, tizanidine); and/or chemicals with vasoconstrictor properties including, but not limited to corticosteroids, ephedrine, pseudoephedrine, caffeine, escin; botanical extracts with vasoconstrictor properties including but not limited to extracts from ephedra, phedra sinica, hamamelis viginiana, hydrastis canadensis, lycopus virginicus, aspidosperma quebracho, cytisus scoparius, raphanus sativus linn [radish leave extracts], horse chestnut extracts, etc.); nasal and/or sinus decongestants; chemicals or botanical extracts improving appearance of hemorrhagic (purpuric) skin lesions; anti-histamines; anti-microbials and/or antibiotics (including, but not limited to, gentamicin, penicillins, cephalosporins, quinolones, ciprofloxacin, and/or novobiocin); chemicals with anti-fungal properties (including but not limited to ketoconazole, naftifine hydrochloride, oxiconazole nitrate, sulconazole nitrate, urea, terbinafine hydrochloride, and/or selenium sulfide); chemicals with anti-mite properties (including but not limited to crotamiton, ivermectin, and/or permethrin); chemicals or botanical extracts with anti-acne properties (including, but not limited to benzoyl peroxide, salicylic acid, sulfur, retinoic acid, tretinoin; alpha-hydroxy acids; anti-microbials, etc.); chemicals or botanical extracts with anti-androgen properties (e.g., androgen receptor blockers, inhibitors of circulating androgens by affecting the ovarial function (i.e., oral contraceptives), inhibitors of circulating androgens by affecting the pituitary (i.e., gonadotropin-releasing hormone agonists and dopamine agonists), inhibitors of the adrenal function, and inhibitors of peripheral androgen metabolism (e.g., 5-reductase inhibitors)); chemicals or botanical extracts with anti-parasitic properties; chemicals or botanical extracts with anti-dandruff properties; chemicals or botanical extracts with anti-seborrheic properties; keratolytic agents or botanical extracts with keratolytic properties (including, but not limited to alpha-hydroxy acids; urea, salicylic acid, etc.); serine protease inhibitors; astringents; anti-acne chemicals; sunscreens; antioxidants (including but not limited to vitamin C, vitamin E, ferulic acid, polyphenols, green tea extract, coffee berry extract, plant extracts with polyphenols, and/or lipoic acid); hair growth regulators; anti-atrophy actives, anti-cellulite actives, oil control agents; vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E and vitamin K, creatine, carnitine and essential fatty acids such as linoleic acid and linolenic acid; and anti-microbial preservatives or botanical extracts with anti-microbial properties (e.g., parbens, phenoxyethanol, benzoic acid, sorbic acid, ethylhexylglycerin, etc.).

More specifically, the combination of said antimicrobial sequestering compound with a rosacea inhibitory agent, an anti-inflammatory agent, an anti-microbial agent, and/or a vasoconstrictor may lead to an enhanced efficacy as compared to the use of the said antimicrobial sequestering compound alone, or the use of rosacea inhibitory agent alone, or the use of anti-inflammatory agent alone, or the use of anti-microbial agent alone, or the use of vasoconstrictor alone. The enhanced efficacy can be additive (the sum of efficacies of the individual agents alone), or it can be synergistic (larger than the sum of efficacies of the individual agents alone). For example, synergisms in efficiency for treatment of rosacea are expected when combining said antimicrobial sequestering compound with either metronidazole, sodium sulfacetamide, clindamycin phosphate, or azelaic acid.

These compositions may further comprise one or more of the following: caffeine; theobromine; theophylline; glycerin; zinc salts (including, but not limited to, zinc sulfate, zinc chloride, zinc glycinate, zinc gluconate, zinc-histidine, zinc L-2-pyrrolidone-5-carboxylate [zinc PCA], zinc salt of linoleic acid, zinc salt of linolenic acid, zinc salt of azelaic acid, zinc peptides and/or zinc oxide); copper salts (including, but not limited to, copper sulfate, copper chloride, copper glycinate, copper gluconate, copper-histidine, copper L-2-pyrrolidone-5-carboxylate [copper PCA], copper salt of linoleic acid, copper salt of linolenic acid, copper salt of azelaic acid, copper peptides); anti-wrinkle and/or anti-aging agents; retinoic acid; tretinoin; isotretinoin; retinol; Vitamin A; fatty acid and/or fatty acid esters (including, but not limited to, linoleic acid and linolenic acid); plant and/or vegetable extracts or concentrates such as lyophilisates, evaporates, filtrates, supercritical fluid (e.g., carbon dioxide) extracts, and distillates thereof (including, but are not limited to, extracts from yeast (e.g., baker's yeast), brewer spent grain (byproduct of beer brewing consisting of the residue of malt and grain which remains in the mash-kettle after the mashing and lautering process), barley, soybean, soybean milk, oat, lavender, licorice, ginger, ginseng, turmeric, apple, sea whip, algae, aloe barbadensis leaves, cactus (e.g., leave, stem), green tea, black tea, white tea, chamomile, birch tree, mint, boswellia, etc.); vegetable oils; saturated dicarboxylic acids; emollients, humectants and/or skin moisturizers; skin protectants; skin barrier enhancers; skin penetration enhancers; skin conditioning agents; minerals and/or make-up compounds suitable for cosmetic use; optical blurring agents (i.e., mica, talc, special polymer spheres, fluorophores, etc.) suitable for cosmetic use; color additives (e.g., FD&C Green No. 3, D&C Green No. 5, chlorophyll, copper chlorophyllin, etc.) suitable for cosmetic use; skin lightening and/or brightening agents; amino acids; peptides; polypeptides, growth factors and/or cytokines including, but not limited to, TGF-betas, EGF, PDGF, and IL-10; cell lysates (e.g., dermal fibroblast cell lysate, stem cell lysate, processed skin cell proteins (PSP®), etc.); conditioned cell culture mediums (e.g., conditioned cell culture medium from dermal fibroblasts, conditioned cell culture medium from stem cells, Nouricel-MD®, etc.), stem cell extracts and/or components from stem cells including stem cell lysates; ingredients stimulating epidermal or other stem cells; and any derivatives, combinations, or mixtures thereof.

In particular embodiments, the compositions of the present invention may comprise a wide range of additional ingredients. The 2010 International Cosmetic Ingredient Dictionary and Handbook, 13th edition and the 2009 Cosmetic Bench Reference—Directory of Cosmetic Ingredients (published by Cosmetics & Toiletries; ISBN-13: 978-1-932633-43-6) describes a wide variety of non-limiting cosmetic and pharmaceutical ingredients commonly used in the skin care and dermatology industry, which are available for use in the present invention. Exemplary functional classes include (see 2009 Cosmetic Bench Reference; pages 37 to 86), but are not limited to, abrasive, absorbent powder, absorption base, acidulent, activator, adhesion promotor, AHA, alcohol, alcohol ester, analgesic, anesthetic, antacid, anti-acne, anti-aging, anti-bacterial, anti-cracking, anti-cellulite, anti-dandruff, anti-foam, anti-inflammatory, anti-irritant, anti-microbial, antioxidant, antiperspirant, anti-pruritic, antiseptic, antistat agent, astringent, barrier agent, binding agent, hair beaching agent, botanical, buffer agent, calming agent, carrier agent, chelating agent, circulatory stimulant agent, cleansing agent, co-emulsifier agent, colorant, conditioning agent, controlled release agent, cooling agent, co-solvent, coupling agent, denaturant, deodorant, depilatory agent, detangler agent, detergent, disinfectant, dispersant, dye stabilizer, emollient, emulsifier, emulsion stabilizer, enzyme, essential oil, exfoliant, fiber, film former, fixative, flavor, foam booster, foam stabilizer, foaming agent, fragrance, fungicide, gellant, glosser, hair colorant, hair conditioner, hair-set polymer, humectant, hydrophobic agent, hydrotropic agents intermediate agent, lathering agent, lubricant, moisture barrier agent, moisturizer, neutralizer, odor-masking agent, oil absorbent agent, ointment base, opacifier, organosilicone, oxidant, oxygen carrier, pearlant agent, perfume solvent, perfume stabilizer, peroxide stabilizer, pigment, plasticizer, polish agent, polymer, polymer film former, powder, preservative, propellant, protein, reducing agent, re-fatting agent, regenerator, resin, scrub agent, sabostatic agent, sequestrant, silicone, silicone replacement, skin calming agent, skin clarifier, skin cleanser, skin conditioner, skin healing agent, skin lightening agent, skin protectant agent, skin purifier agent, skin smoothing agent, skin soothing agent, skin treatment agent, solubilizer, solvent, SPF booster, spreading agent, stabilizer, stimulant agent, sunless tanning agent, sunscreen UVA, sunscreen UVB, super-fatting agent, surfactant, amphoteric surfactant, anionic surfactant, cationic surfactant, non-ionic surfactant, silicone surfactant, suspending agent, sweetener, tanning accelerator, thickener, thixotrope, toner, tonic agent, topical delivery system, vegetable oil, viscosity stabilizer, vitamin, water proofing agent, wax, wetting agent, whitening agent, and wound healing agent. The 2009 Cosmetic Bench Reference (pages 37 to 86) provides examples of ingredient for functional class. This information is also available; and is regularly updated by the addition of new ingredients (and functional classes), at http://dir.cosmeticsandtoiletries.com/search/cbr_ing.html.

Skin conditioning agent include, for example, a substance that enhances the appearance of dry, aged or damaged skin, as well as a material that adheres to the skin to reduce flaking, restore suppleness, and generally improve the appearance of skin. Representative examples of a skin conditioning agent that may be used include: acetyl cysteine, N-acetyl dihydrosphingosine, acrylates/behenyl acrylate/dimethicone acrylate copolymer, adenosine, adenosine cyclic phosphate, adenosine phosphate, adenosine triphosphate, alanine, albumen, algae extract, allantoin and derivatives, aloe barbadensis extracts, amyloglucosidase, arbutin, arginine, bromelain, buttermilk powder, butylene glycol, calcium gluconate, carbocysteine, carnosine, beta-carotene, casein, catalase, cephalins, ceramides, chamomilla recutita (matricaria) flower extract, cholecalciferol, cholesteryl esters, coco-betaine, corn starch modified, crystallins, cycloethoxymethicone, cysteine DNA, cytochrome C, darutoside, dextran sulfate, dimethicone copolyols, dimethylsilanol hyaluronate, elastin, elastin amino acids, ergocalciferol, ergosterol, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, kinetin, kinetin esters, and/or derivatives thereof. Other non-limiting examples of a skin conditioning agent that may be included in the compositions include lactoferrin, lanosterol, lecithin, lysolecithin, linoleic acid, linolenic acid, lipase, lysine, lysozyme, malt extract, maltodextrin, melanin, methionine, niacin, niacinamide, oat amino acids, oryzanol, palmitoyl hydrolyzed proteins, pancreatin, papain, polyethylene glycol, pepsin, phospholipids, phytosterols, placental enzymes, placental lipids, pyridoxal 5-phosphate, quercetin, resorcinol acetate, riboflavin, saccharomyces lysate extract, silk amino acids, sphingolipids, stearamidopropyl betaine, stearyl palmitate, tocopherol, tocopheryl acetate, tocopheryl linoleate, ubiquinone, vitis vinifera (grape) seed oil, wheat amino acids, xanthan gum, and/or zinc gluconate. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Suitable skin protectant agents for use in the compositions described herein include, for example, a compound that protects injured or exposed skin or mucous membrane surfaces from harmful or irritating external compounds. Representative examples include algae extract, allantoin, camellia sinensis leaf extract, cerebrosides, dimethicone, glucuronolactone, glycerin, kaolin, lanolin, malt extract, mineral oil, petrolatum, white petrolatum, potassium gluconate, colloidal oat meal, calamine, coca butter, starch, zinc oxide, zinc carbonate, zinc acetate, and/or talc. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Suitable skin lightening agents include, but are not limited to, ascorbic acid and derivatives thereof; kojic acid and derivatives thereof; phenylethyl resorcinol, L-leucine, glycine, disodium glycerophosphate, undecenoyl phenylalanine, arbutin, hydroquinone; azelaic acid; resveratrol, oxyresveratrol, polyphenols, various plant extracts, such as those from licorice, grape seed, and/or bear berry; and/or any ingredient or combination thereof as taken from WO 2010-083368 Patent Application (enclosed herein as reference). Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

One or more emollients may also be included in the topical compositions described herein. An emollient generally refers to an ingredient that can help skin maintain a soft, smooth, and pliable appearance. Emollients typically remain on the skin surface, or in the stratum corneum, and act as a moisturizer, or lubricant and reduce flaking. Some examples of emollients include acetyl arginine, acetylated lanolin, algae extract, apricot kernel oil polyethylene glycol-6 esters, avocado oil polyethylene glycol-11 esters, bis-polyethylene glycol-4 dimethicone, butoxyethyl stearate, glycol esters, alkyl lactates, caprylyl glycol, cetyl esters, cetyl laurate, coconut oil polyethylene glycol-10 esters, alkyl tartrates, diethyl sebacate, dihydrocholesteryl butyrate, dimethiconol, dimyristyl tartrate, disteareth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, palm oil, coconut oil, myreth-3 palmitate, octyldecanol, octyldodecanol, odontella aurita oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, petrolatum, silicon oils including but not limited to caprylyl methicone, and/or tocopheryl glucoside. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Humectants are ingredients that help maintain moisture levels in skin. Examples of humectants include acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, hydrolyzed proteins, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, butylene glycol, sodium pyrollidone carboxylic acid (PCA), sorbitol, sucrose, dextran sulfate (i.e., of any molecular weight), hyaluronic acid, and/or urea. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

The compositions disclosed herein can be formulated as an emulsion. Either a water-in-oil, or an oil-in-water emulsion may be formulated. Examples of suitable surfactants and emulsifying agents include nonionic ethoxylated and nonethoxylated surfactants, abietic acid, almond oil polyethylene glycol, beeswax, butylglucoside caprate, glycol ester, alkyl phosphate, caprylic/capric triglyceride polyethylene glycol4 esters, ceteareth-7, cetyl alcohol, cetyl phosphate, corn oil polyethylene glycol esters, dextrin laurate, dilaureth-7 citrate, dimyristyl phosphate, glycereth-17 cocoate, glyceryl erucate, glyceryl laurate, hydrogenated castor oil polyethylene glycol esters, isosteareth-11 carboxylic acid, lecithin, lysolecithin, nonoxynol-9, octyldodeceth-20, palm glyceride, polyethylene glycol diisostearate, polyethylene glycol stearamine, poloxamines, potassium linoleate, raffinose myristate, sodium caproyl lactylate, sodium caprylate, sodium cocoate, sodium isostearate, sodium tocopheryl phosphate, steareths, and/or trideceths. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

In addition, thickening agents suitable for inclusion in a composition or formulation described herein include those agents commonly used in skin care preparations. (See, e.g., U.S. Pat. No. 6,444,647, incorporated herein by reference). More specifically, such examples include acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, magnesium alginate, methylcellulose, microcrystalline cellulose, pectin, various polyethylene glycol's, polyacrylic acid, polymethacrylic acid, polyvinyl alcohol, various polypropylene glycols, sodium acrylates copolymer, sodium carrageenan, xanthan gum, and/or yeast beta-glucan. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Carboxylic acid polymers are cross-linked compounds containing one or more monomers derived from acrylic acid, substituted acrylic acids, and salts and esters of these acrylic acids and the substituted acrylic acids, wherein the cross-linking agent contains two or more carbon-carbon double bonds and is derived from a polyhydric alcohol. Polymers useful in the present invention are more fully described in U.S. Pat. Nos. 5,087,445; 4,509,949; 2,798,053; and in CTFA International Cosmetic Ingredient Dictionary, Fourth Edition, 1991, pp. 12 and 80, each of which are herein incorporated by reference. Examples of commercially available carboxylic acid polymers useful herein include the carbomers, which are homopolymers of acrylic acid cross-linked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the cross-linking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich. In some embodiments, examples of preferred carboxylic acid polymer thickeners useful herein include those selected from carbomers, acrylates/$C_{10-30}$ alkyl acrylate crosspolymers, and mixtures thereof. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Any of the compositions described herein can also optionally contain cross-linked polyacrylate polymers, which are useful as thickeners or gelling agents including both cationic and nonionic polymers, with the cationics being generally preferred. Examples of useful cross-linked nonionic polyacrylate polymers and cross-linked cationic polyacrylate polymers are described in U.S. Pat. Nos. 5,100,660; 4,849,484; 4,835,206; 4,628,078; 4,599,379 and in EP 228,868, each of which are herein incorporated by reference in their entireties.

In addition, the compositions of the present invention can also optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Moreover, a wide variety of polysaccharides are useful herein as thickening agents. Non-limiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10-30}$ straight chain or branched chain alkyl group through an ether linkage. Typically these polymers are ethers of $C_{10-30}$ straight or branched chain alcohols with hydroxyalkylcelluloses. Examples of alkyl groups useful herein include those selected from stearyl, isostearyl, lauryl, myristyl, cetyl, isocetyl, cocoyl (i.e., alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.). Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, dextran sulfate, sodium carrageenan, tragacanth gum, xanthan gum, and/or mixtures thereof. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Preferred compositions of the present invention include a thickening agent selected from carboxylic acid polymers, cross-linked polyacrylate polymers, polyacrylamide polymers, and mixtures thereof, more preferably selected from carboxylic acid polymers, polyacrylamide polymers, and mixtures thereof.

As used herein, the term "substantially free" as used herein means that the composition of interest is present in the composition in an amount less than 0.1% per weight, preferably less than 0.05% by weight, and most preferably less than 0.01% per weight.

Preferably, the compositions of the invention are substantially free of cationic polymers such as those polymers based on 5 or 6 carbon sugars and derivatives, which have been made cationic by engrafting of cationic moieties on the polysaccharide backbone. They may be composed of one type of sugar or of more than one type, i.e., copolymers of the above derivatives and cationic materials. The monomers may be in straight chain or branched chain geometric arrangements.

Exemplary cationic polymers that are excluded from the compositions of the invention include, but are not limited to, chitosan; DEAE-dextran; cationic guar gum; cationic polysaccharides (e.g., cationic celluloses); cationic copolymers of saccharides and synthetic cationic monomers; cationic polyakylene imines; cationic ethoxy polyalkylene imines; hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae. Additional examples can be found in the The International Cosmetic Ingredient Dictionary and Handbook, the Cosmetic Bench Reference—Directory of Cosmetic Ingredients, the books provided by the United States Pharmacopeia (USP) and the National Formulary (NF), and other references for cosmetic and pharmaceutical ingredients known in the art.

Furthermore, the compositions are also preferably substantially free composition is substantially free of aluminum or aluminum ions.

The examples as set forth herein are meant to exemplify the various aspects of carrying out the invention and are not intended to limit the invention in any way. Unless otherwise specified, it is to be understood that the concentrations of the component ingredients in the compositions of the invention are in %, w/w, based on the total weight of the composition.

Example 1a

Preparation of Composition Suitable for Topical Application with 0.1 w % Sodium Salt of Dextran Sulfate of Average Molecular Weight of about 8000 Grams Per Mol In this example, the composition additionally contains hydroxypropyl starch phosphate and Aristoflex HMB. The composition also contains glycerin, caffeine, and zinc PCA together with the other ingredients forming a composition suitable for topical use. In this composition, the following ingredients are mixed together as stated below in order to obtain a stable composition, which is suitable for topical use:

| Phase | Ingredient (Trade Name) | INCI Name | Supplier | % by weight (% w) |
|---|---|---|---|---|
| A | Water | Water (Aqua) | | 60.30 |
| A | Na2EDTA | Disodium EDTA | Akzo/DeWolf | 0.1 |
| A | Keltrol CG-SFT | Xanthan Gum | CP Kelco/ Univar | 0.25 |

| Phase | Ingredient (Trade Name) | INCI Name | Supplier | % by weight (% w) |
|---|---|---|---|---|
| A | Aristoflex HMB | Ammonium Acryloyldimethyltaurate/ Beheneth-25 Methacrylate Crosspolymer | Clariant/ Essential Ingredients | 1.25 |
| A | Structure XL | Hydroxypropyl Starch Phosphate | National Starch | 1.5 |
| B | Water | | | 14 |
| B | Oristract CF | Caffeine | Orient Stars | 1.5 |
| B | Dextran Sulfate Sodium Salt (Av. M.W. about 8000) | Dextran Sodium Sulfate | MP Biomedical/ Spectrum | 0.1 |
| B | Ajidew ZN-100 | Zinc PCA | Ajinomoto | 1 |
| B1 | Glycerin 99.7% | Glycerin | Acme-Hardesty | 15 |
| B1 | Phenoxetol | Phenoxyethanol | Clariant/ Essential Ingredients | 1 |
| C | Structure XL | Hydroxypropyl Starch Phosphate | National Starch | 1 |
| D | DC Toray FZ-3196 | Caprylyl Methicone | Dow Corning/ Univar | 3 |

Phase A: Dissolve Na2EDTA into agitation Phase A water. Mix until uniform. Sprinkle Keltrol CG-SFT slowly into batch. Mix until fully hydrated. Sprinkle Aristoflex HMB into agitating Phase A and mix until fully hydrated. Sprinkle Structure XL into agitating Phase A and mix until fully dispersed.
Phase B: Combine Phase B in a separate vessel. Add Phase B to batch with mixing.
Phase C: Add Phase C to batch with mixing, mix until uniform.
Phase D: In a separate vessel, combine Phase D ingredients, mix until uniform and slowly add to batch and mix until uniform. Final composition of pH 4.6 and 11000 cps viscosity.

Example 1b

Preparation of Composition Suitable for Topical Application with 0.25 w % Sodium Salt of Dextran Sulfate of Average Molecular Weight of about 8000 Grams Per Mol In this example, the composition additionally contains hydroxypropyl starch phosphate and Aristoflex HMB. The composition also contains glycerin, caffeine, and zinc PCA together with the other ingredients forming a composition suitable for topical use. In this composition, the following ingredients are mixed together as stated below in order to obtain a stable composition, which is suitable for topical use:

| Phase | Ingredient (Trade Name) | INCI Name | Supplier | % by weight (% w) |
|---|---|---|---|---|
| A | Water | Water (Aqua) | | 60.30 |
| A | Na2EDTA | Disodium EDTA | Akzo/DeWolf | 0.1 |
| A | Keltrol CG-SFT | Xanthan Gum | CP Kelco/ Univar | 0.25 |
| A | Aristoflex HMB | Ammonium Acryloyldimethyltaurate/ Beheneth-25 Methacrylate Crosspolymer | Clariant/ Essential Ingredients | 1.25 |
| A | Structure XL | Hydroxypropyl Starch Phosphate | National Starch | 1.5 |
| B | Water | | | 13.85 |
| B | Oristract CF | Caffeine | Orient Stars | 1.5 |
| B | Dextran Sulfate Sodium Salt (Av. M.W. about 8000) | Dextran Sodium Sulfate | MP Biomedical/ Spectrum | 0.25 |
| B | Ajidew ZN-100 | Zinc PCA | Ajinomoto | 1 |
| B1 | Glycerin 99.7% | Glycerin | Acme-Hardesty | 15 |
| B1 | Phenoxetol | Phenoxyethanol | Clariant/ Essential Ingredients | 1 |
| C | Structure XL | Hydroxypropyl Starch Phosphate | National Starch | 1 |
| D | DC Toray FZ-3196 | Caprylyl Methicone | Dow Corning/ Univar | 3 |

Phase A: Dissolve Na2EDTA into agitation Phase A water. Mix until uniform. Sprinkle Keltrol CG-SFT slowly into batch. Mix until fully hydrated. Sprinkle Aristoflex HMB into agitating Phase A and mix until fully hydrated. Sprinkle Structure XL into agitating Phase A and mix until fully dispersed.
Phase B: Combine Phase B in a separate vessel. Add Phase B to batch with mixing.
Phase C: Add Phase C to batch with mixing, mix until uniform.
Phase D: In a separate vessel, combine Phase D ingredients, mix until uniform and slowly add to batch and mix until uniform. Final composition is of approximately pH 4.5 and 10000 cps viscosity.

Example 1c

Preparation of Composition Suitable for Topical Application with 0.5 w % Sodium Salt of Dextran Sulfate of Average Molecular Weight of about 8000 Grams Per Mol In this example, the composition additionally contains hydroxypropyl starch phosphate. The composition also contains glycerin, caffeine, and zinc PCA together with the other ingredients forming a composition suitable for topical use. In this composition, the following ingredients are mixed together as stated below in order to obtain a stable composition, which is suitable for topical use:

| Phase | Ingredient (Trade Name) | INCI Name | Supplier(s) | % by weight (% w) |
|---|---|---|---|---|
| A | Water | Water (Aqua) | | 60.04 |
| A | Na2EDTA | Disodium EDTA | Akzo/DeWolf | 0.1 |
| A | Keltrol CG-SFT | Xanthan Gum | CP Kelco/ Univar | 0.25 |
| A | Structure XL | Hydroxypropyl Starch Phosphate | National Starch | 1.0 |
| A | Simulgel INS 100 | Hydroxyethyl Acrylate/Sodium Acryloyldimethyl Taurate Copolymer (and) Isohexadecane (and) Polysorbate-60 | Seppic | 1.0 |
| B | Water | | | 15 |
| B | Oristract CF | Caffeine | Orient Stars | 1.5 |
| B | Dextran Sulfate Sodium Salt (av. M.W. about 8000) | Dextran Sodium Sulfate | MP Biomedical/ Spectrum | 0.5 |
| B | Ajidew ZN-100 | Zinc PCA | Ajinomoto | 1 |
| B1 | Elestab CPN Ultra Pure | Chlorphenesin | Cognis | 0.2 |
| B1 | Glycerin 99.7% | Glycerin | Acme-Hardesty | 15 |
| B1 | Phenoxetol | Phenoxyethanol | Clariant/ Essential Ingredients | 0.5 |

-continued

| Phase | Ingredient (Trade Name) | INCI Name | Supplier(s) | % by weight (% w) |
|---|---|---|---|---|
| C | Structure XL | Hydroxypropyl Starch Phosphate | National Starch | 1.5 |
| C | Simulgel INS 100 | Hydroxyethyl Acrylate/Sodium Acryloyldimethyl Taurate Copolymer (and) Isohexadecane (and) Polysorbate-60 | Seppic | 0.41 |
| D | DC Toray FZ-3196 | Caprylyl Methicone | Dow Corning/Univar | 2 |

Phase A: Dissolve Na2EDTA into agitating Phase A water. Mix until uniform. Sprinkle Keltrol slowly into batch. Mix until fully hydrated. Sprinkle Structure XL into agitating Phase A water. Mix until fully dispersed, and homogenize at 3500 RPM for 5-6 minutes. Add Simulgel INS 100 and mix until uniform, then homogenize for about 4 minutes at 3500 RPM.
Phase B: Combine Phase B ingredients, one by one in a separate vessel while heating to 50-53° Celsius (not higher than 55° Celsius).
Phase B1: In a separate vessel combine Phase B1 ingredients and heat to 40° Celsius. Mix until powder is dispersed. Add Phase B1 to Phase B and mix until clear. Cool to 30° Celsius and add combined Phase B/B1 to batch. Mix until uniform.
Phase C: Add Phase C to batch one by one to raise viscosity, homogenize after adding the Structure Xl and again after adding the Simulgel INS 100.
Phase D: Add Phase D ingredients to batch and mix until uniform.

Example 2

Clinical Study with Rosacea Patients

Study Design & Methods:

Rosacea patients between 12 to 85 years of age applied a composition containing dextran sulfate (i.e., the composition described in Example 1c) twice daily (morning and evening) on the face after cleansing the face with a gentle skin cleanser over a period of about 8 weeks. The following assessments or evaluations were performed before the treatment (Visit 1) and during the treatment period after about 2 weeks (Visit 2), about 4 weeks (Visit 3) and about 8 weeks (Visit 4):

Investigator's Tolerability Assessment:

Tolerability including burning/stinging/tingling, pruritis, dryness, scaling/peeling and atrophy were evaluated of the face by the investigator (i.e., dermatologist) according to the following scale: 0=none, 1=mild, 2=moderate, 3=severe.

Furthermore, any adverse events experienced by subject during the study period, whether related to the treatment or not, were recorded.

Investigator's Global Assessment (Iga) for Papulopustular Rosacea:

Assessment of overall skin conditions of the face was performed by the investigator (i.e., dermatologist) according to the following scoring system:

| Score | Grade | Description Redness | Description Inflammatory Lesions |
|---|---|---|---|
| 0 | Clear | No or almost no residual erythema; mild to moderate degree of telangiectasia may be present | No papules and/or pustules |
| 1 | Minimal | Residual to mild erythema; mild to moderate degree of telangiectasia may be present | Rare papules and/or pustules |
| 2 | Mild | Mild erythema; mild to moderate degree of telangiectasia may be present | Few papules and/or pustules |
| 3 | Mild to Moderate | Mild to moderate erythema; mild to moderate degree of telangiectasia may be present | Distinct number of papules and/or pustules |
| 4 | Moderate | Moderate erythema; mild to moderate degree of telangiectasia may be present | Pronounced number of papules and/or pustules |
| 5 | Moderate to severe | Moderate to severe erythema; moderate degree of telangiectasia may be present | Many papules and/or pustules, occasionally with large inflamed lesions |
| 6 | Severe | Severe erythema; moderate to severe degree of telangiectasia may be present | Numerous papules and/or pustules, occasionally with confluent areas of inflamed lesions |

Inflammatory Lesion Count for Papulopustular Rosacea:
Count of total number of inflammatory lesions (papules and pustules) on the face by the investigator (i.e., dermatologist).

Investigator Assessment of Redness/Erythema and Telangiectasia:

Evaluation of the severity of both redness/erythema and telangiectasia on the face by the investigator (i.e., dermatologist) according to the following scale:

| REDNESS/ERYTHEMA | | TELANGIECTASIA | |
|---|---|---|---|
| Score Grade | Redness/Erythema Description | Score Grade | Telangiectasia Description |
| 0 Clear or almost clear | No visible redness/erythema or minimal redness/erythema | 0 None | No visible telangiectasia |

| REDNESS/ERYTHEMA | | TELANGIECTASIA | | |
|---|---|---|---|---|
| Score | Grade | Redness/Erythema Description | Score | Grade | Telangiectasia Description |
| 1 | Mild | Slight redness/erythema either centrofacial or generalized to whole face | 1 | Mild | Only few fine vessels discernible, involves 10% or less of the facial area |
| 2 | Moderate | Pronounced redness/erythema either centrofacial or generalized to whole face | 2 | Moderate | Multiple fine vessels few and/or few large vessels discernible, involves 10-30% of the facial area |
| 3 | Severe | Severe redness/erythema/ red to purple hue, either centrofacial or generalized to whole face | 3 | Severe | Many fine vessels and/or large vessels discernible, involves more than 30% of the facial area |

Investigator Rating of Overall Improvement.

The assessment consisted of the rating of the overall improvement of rosacea based on a comparison of the rosacea severity from baseline using a 7-point scale reflecting the degree of clearance of disease signs and symptoms by the investigator (i.e., dermatologist) according to the following scale: 0=complete remission, 1=excellent improvement (75-99%), 2=marked improvement (50-74%), 3=moderate improvement (25-49%), 4=slight improvement (1-24%), 5=no change, 6=deterioration.

Clinical Photography:

Clinical photographs were taken at all visits utilizing standardized conditions for all subjects. The skin must be cleansed prior to photography to remove any topical products such as powder makeup, lipstick/gloss and mascara. The settings for the exposure, lighting, flash, and focal length were maintained constant over the course of the study. Subjects were photographed using a clinical photographic system in a consistent position. It was also important to capture the area under controlled conditions, utilizing neutral expressions and neutral angles (e.g., avoiding hypo- or hyperextension of the neck) so as to enable comparison over time. As each photograph is being taken, it was viewed to ensure that it is in focus and is similar to its baseline counterpart in all technical aspects, including lighting, distance and angle. Photos were taken from three angles to enable the improvement to be clearly noticed: full frontal (0°) and at profile from the left (45°) and from the right side (−45). Photos were taken at controlled distances under standard room lighting. In case possible, cross-polarized, parallel-polarized and visible light images were acquired along with both blue fluorescence and ultraviolet fluorescence images.

Study Results:

The composition (i.e., the composition described in Example 1c) containing dextran sulfate (e.g., sodium salt of dextran sulfate) of an average molecular weight of about 8000 grams per mol was evaluated in a clinical study with fourteen subjects with erythematotelangiectatic rosacea (also called subtype I rosacea) and two subjects with papulopustular rosacea (subtype II). The study included male and female subjects. All subjects experienced facial redness and additionally also telangiectasia.

The composition was shown to reduce facial redness (or erythema) by 27% after about two weeks, by 42% after about four weeks, and by 43% after about 8 weeks of twice daily topical application of the composition to the face as compared to before treatment.

In addition, the composition was shown to also reduce telangiectasia by 21% after about two weeks, by 26% after about four weeks, and by 34% after about 8 weeks of twice daily topical application of the composition to the face as compared to before treatment.

The composition was also shown to also reduce the papulopustular overall severity by 23% after about two weeks, by 43% after about four weeks, and by 42% after about 8 weeks of twice daily topical application of the composition to the face as compared to before treatment.

Likewise, the composition was shown to also decrease the number of inflammatory lesions by 12% after about two weeks, by 72% after about four weeks, and by 44% after about 8 weeks of twice daily topical application of the composition to the face as compared to before treatment.

As assessed by the investigator, at least moderate improvements in symptoms of rosacea were observed in 31% of the subjects after about 2 weeks, 60% of the subjects after about 4 weeks, and 64% of the subjects after about 8 weeks of twice daily topical application of the composition to the face as compared to before treatment. Moreover, at least marked improvements in symptoms of rosacea were observed in 13% of the subjects after about 2 weeks, 13% of the subjects after about 4 weeks, and 29% of the subjects after about 8 weeks of twice daily topical application of the composition to the face as compared to before treatment.

Moreover, the composition was well tolerated and only few subjects reported some minor burning and dryness during the treatment period with the composition. No subject reported any allergy or contact allergy, and there was no evidence of immunotoxic effects to the composition, or to sodium dextran sulfate, or to other antimicrobial sequestering agents (i.e., Structure XL).

Example 3a

Clinical Study with Psoriasis Patients

Psoriasis patients older than 12 years of age applied a composition containing dextran sulfate (i.e., any of the compositions described in Example 1) once to twice daily (morning and/or evening) on the affected skin area over a period of about 4 to 16 weeks. Evaluations of clinical signs included assessment of the severity of the lesions for each of the signs of redness, thickness and scaliness, using a 5-category scale ranging from no signs/symptoms (score 0) to very severe signs/symptoms (score 4). The sum of these 3 scores (redness, thickness and scaliness) gave a total sign score ranging from 0 (no symptoms) to 12 (very severe symptoms).

On the Investigator's Global Assessment (IGA), disease severity was assessed using a 6-category scale ('absence of', 'very mild', 'mild', 'moderate', 'severe', 'very severe' disease). Patients with disease severity classified as 'absence of disease' or 'very mild disease' were rated as having 'controlled disease'. Patients assessed their overall response to treatment using a 7-category scale ranging from 'worse' to 'cleared'. Patients with treatment response classified as 'marked improvement', 'almost clear' or 'cleared' were rated as achieving 'treatment success'.

The composition was shown to reduce redness, thickness and scaliness of the psoriasis lesions, as well as to reduce overall disease severity as assessed by IGA after about 4 to 16 weeks of once to twice daily topical application of the compositions to the affected skin site on the face and other body regions affected by psoriasis.

The composition was well tolerated. No subject reported any allergy or contact allergy and there was no evidence of immunotoxic effects to the composition, or to sodium dextran sulfate, or to other antimicrobial sequestering agents (i.e., Structure XL, Aristoflex HMB).

Example 3b

Clinical Study with Acne Vulgaris Patients

Acne (i.e., acne vulgaris) patients older than 6 years of age applied a composition containing dextran sulfate (e.g., any of the compositions described in Example 1) once to twice daily (morning and/or evening) over a period of about 4 to 16 weeks. The following assessments were performed before the treatment and during and at the end of the treatment period: IGA (clear, almost clear, mild, moderate, severe, very severe), overall disease severity, lesion counts (inflammatory, non-inflammatory, total), assessment of the severity of the lesions (as described in Journal of Drugs in Dermatology 9:131-36 (2010) (incorporated herein as reference)).

The composition was shown to reduce the number and severity of inflammatory and non-inflammatory lesions, as well as to reduce the overall disease severity and to improve IGA after about 4 to 16 weeks of once to twice daily topical application of the composition to the face or other and other skin regions affected by acne lesions.

The composition was well tolerated and only few subjects reported some minor and transitory burning and dryness during the treatment period with the composition. No subject reported any allergy or contact allergy and there was no evidence of immunotoxic effects to the composition, or to sodium dextran sulfate, or to other antimicrobial sequestering agents (i.e., Structure XL, Aristoflex HMB).

Example 3c

Clinical Study with Atopic Dermatitis (Eczema) Patients

Atopic dermatitis patients older than 12 years of age applied the compositions containing dextran sulfate (i.e., any of the compositions described in Example 1) once to twice daily (morning and evening) on the affected skin area over a period of about 4 to 16 weeks. The following assessments were performed before the treatment, during and at the end of the treatment period: IGA (clear, almost clear, mild, moderate, severe, very severe) and overall disease severity.

The composition was shown to reduce the overall disease severity and to improve IGA after about 4 to 16 weeks of once to twice daily topical application of the composition to the face or other and other skin regions affected by atopic dermatitis (eczema). The composition was well tolerated. No subject reported any allergy or contact allergy and there was no evidence of immunotoxic effects to the composition, or to sodium dextran sulfate, or to other antimicrobial sequestering agents (i.e., Structure XL, Aristoflex HMB).

Example 4a

Preparation Sulfated Polysaccharides by Chemical Synthesis

Sulfated Polysaccharides can be synthesized as has been previously described. (See Trends in Glycoscience and Glycotechnology 15:29-46 (2003); Angew. Chem. Int. Ed. 43:3118-33 (incorporated herein by reference)). For instance, various methods for sulfonation of hydroxyl groups of polysaccharides involving chlorosulfonic acid-pyridine complex, sulfuric acid mediated by dicyclohexyl-carbodiimide (see J. Carbohydr. Chem. 15:449-57 (1996)), sulfur trioxide-trimethylamine complex (see Thromb. Res. 59:749-58 (1990)), and pyridine-sulfur trioxide complex in N,N-dimethylformamide (DMF) as sulfonating reagent have been reported.

Otherwise, a pyridine-sulfur trioxide complex in DMF, in which causes less depolymerization and side reactions can be used to prepare fully sulfated polysaccharides (see Med. Res. Rev. 20:323-49 (2000)). As an example, the polysaccharide was allowed to swell well in dry DMF and was then stirred for 14 h at room temperature. An excess (15 mol/equivalent of available hydroxyl groups in polysaccharides) of sulfur trioxide-pyridine complex was required. The per-sulfonation reaction was carried out with stirring under $N_2$ gas for 6 h at 40° C. The resulting inorganic sulfuric acid was neutralized by an aqueous solution of NaOH. The sulfated polysaccharide was precipitated with cold ethanol, re-dissolved in water, dialyzed against water, and lyophilized. In the case of cellulose, because of the very highly molecular weight of this polysaccharide, a sample was partially depolymerized under mild acid hydrolysis and sulfonation was repeated to afford fully sulfated cellulose. Different conditions were also investigated to obtain other fully sulfated polysaccharides and to prepare oversulfated polysaccharides with different levels of sulfation.

Example 4b

Preparation of Sulfated Polysaccharides by Enzymatic Synthesis

Enzymes "in the pathway" for heparan sulfate biosynthesis have been cloned and expressed, and have been employed in the synthesis of heparan sulfate polysaccharides (see Balagurunathan et al. Nat. Biotechnol. 21:1343-46 (2003); Kuberan et al. J. Am. Chem. Soc. 125:12424-25 (2003); Balagurunathan et al. J. Biol. Chem. 278:52613-21 (2003)). As an example, as described in US Patent Application 20090197308, a method of sulfating a polysaccharide, includes: (a) providing a reaction mixture comprising: at least one O-sulfotransferase (OST) enzyme; and 3'-phosphoadenosine 5'-phosphosulfate (PAPS); (b) incubating a polysaccharide substrate with the reaction mixture, wherein production of the sulfated polysaccharide from the polysaccharide substrate is catalyzed by the OST enzyme with a conversion of the PAPS to adenosine 3',5'-diphosphate (PAP); and (c) providing a reaction condition which modifies PAP to reduce an inhibitory effect of PAP on the polysaccharide sulfation.

Example 5

Fucoidans (See Appl Microbiol Biotechnol 82:1-11 (2009), Molecules 13: 1671-1695 (2008); incorporated herein by reference)

Fucoidans may be obtained from several algae or marine invertebrates like sea cucumber (see Carbohydr Res 255: 225-240 (1994) or sea urchin (see J. Biol Chem 269, 22113-22123 (1994); Glycobiology 9: 927-933 (1999).). The term fucoidan is commonly applied for sulphated complex polysaccharides, often extracted from algae, containing fucose residues in various amounts besides many other monosaccharides, whereas the term sulphated fucan is reserved for sulphated polysaccharides with a regular structure, containing a majority of fucose, which are often extracted from marine animals. However, not all authors stick to this routine and are thus increasing confusion by using words like fucansulfate or the old fucoidin (see Glycobiology 13: 29R-40R (2003)).

In recent years, different brown algae were analyzed for their content of fucoidans including *Pelvetia canaliculata* (see Mar Biotechnol 8:27-39 (2006)), *Fucus vesiculosus* (see J Nat Products 56:478-488 (1993); Nantes Proceedings, pp 122-133 (2002); Translation of Khimiko-Farmatsevticheskii Zhurnal 38:323-326 (2004)), *Sargassum stenophyllum* (see Carbohydr Res 333:281-293. (2001)), *Chorda filum* (see Microbiology (Moscow, Russian Federation) (Translation of Mikrobiologiya) 71:41-47 (2002)), *Ascophyllum nodosum* (see Carbohydr Res 59:531-537 (1977)), *Cladosiphon okamuranus* (see Mar Biotechnol 5:536-544 (2003)), *Dictyota menstrualis* (see Braz J Med Biol Res 37:167-171 (2004)), *Fucus evanescens* (see Microbiology (Moscow, Russian Federation) (Translation of Mikrobiologiya) 71:41-47 (2002); Bull Exp Biol Med (Translation of Byulleten Eksperimental'noi Biologii i Meditsiny) 136:471-473 (2003); Carbohydr Res 341:238-245 (2006)), *Fucus serratus* (see Carbohydr Res 341:238-245 (2006)), *Fucus distichus* (see Carbohydr Res 339:511-517. (2004)), *Kjellmaniella crassifolia* (see Mar Biotechnol 4:399-405 (2002)), *Hizikia fusiforme* (see Carbohydr Res 341:1135-1146 (2006)) and *Analipus japonicus* (see Russ J Bioorgan Chem 33:38-46 (2007)).

To get suitable amounts of fucoidan, the material has to be collected, washed, dried, extracted and freeze dried. If these extraction methods are too harsh, the sulphation pattern may be destroyed and the bio-activity can thus be lost (see Carbohydr Polym 63:224-228 (2006)). Examples of suitable extraction methods and the analysis of the extract are provided in Cryptogam Algol 4:55-62 (1983); Carbohydr Res 194:315-320 (1989); Pharm Chem J (Translation of Khimiko Farmatsevticheskii Zhurnal) 38:323-326 (2004); Glycobiology 17:541-552 (2007) (incorporated herein as references). Fucoidan extracts can also be obtained from diverse commercial sources as illustrated in the following examples (see Bot Mar 43:393-398 (2000); Am J Hematol 78:7-14 (2005); Eur J Neurosci 21:2649-2659 (2005); Synapse (Hoboken, N.J., United States) 60:456-464 (2006)).

Example 6

Sulfated Galactans: the Heterogeneity Arises Mostly Due to Complex Sulfation Patterns (See Glycobiology. 18(12):1016-27 (2008), incorporated herein by reference)

Marine sulfated galactans are widely abundant in red algae. Carrageenans and agarans are the most common sulfated galactans from macroalgae. The origin of the name carrageenan comes from a small village, Carragheen, on the Irish coast, where the carrageenan-bearing seaweed *Chondrus crispus* or "Irish moss" grows (see Brit Food J 96:12-17 (1994)). The word agaran (name proposed by Knutsen et al. (Bot Mar 37:163-169, 1994), see also J Appl Phycol 13:173-184 (2001)) was originally derived from the word "agar," which means jelly in the Malay language (agar-agar). Both of these red algal polysaccharides usually have a linear backbone made of alternating 3-linked β-D-galactopyranose and 4-linked α-galactopyranose residues, showing a "masked repeat" unit of disaccharides similar to the animal glycosaminoglycans. The β-galactoses are always D enantiomers, whereas the α-galactose residues may be present in the D- or L-configuration (see Food Hydrocolloids 12:301-308 (1998)). A substantial portion may also exist in the form of 3,6-anhydro derivatives. Like sulfated fucans from brown algae, considerable structural variation in the red alga sulfated galactans occurs among different species and in samples collected at different environments, or in different seasons of the year (see Carbohydr Res 340:2015-2023 (2005)). Furthermore, various hydroxyl groups may be substituted by a sulfate ester, a methyl group, or pyruvic acid (see Food Hydrocolloids 12:301-308 (1998)). The major structural variation in these polysaccharides is the sulfation pattern.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A topical composition comprising dextran sulfate (about 0.1%-about 0.5% by weight), caffeine (about 1.5% by weight), and zinc salts (about 1% by weight), wherein the composition does not comprise a peptide, polypeptide or protein and the composition is free of aluminum or aluminum ions, and wherein the composition reduces redness by at least about 27% in an individual having rosacea, psoriasis, acne, atopic dermatitis and/or seborrheic dermatitis about 2 weeks after administration of said composition to an individual.

2. The topical composition of claim 1, wherein said composition comprising dextran sulfate at about 0.1% (by weight).

3. The topical composition of claim 1, wherein said composition comprising dextran sulfate at about 0.25% by weight.

4. The topical composition of claim 1, wherein said composition comprising dextran sulfate at about 0.5% by weight.

5. A method for treating in an individual having rosacea, psoriasis, acne, atopic dermatitis and/or seborrheic dermatitis comprising administering topically an effective amount of a composition comprising dextran sulfate (about 0.1%-about 0.5% by weight), caffeine (about 1.5% by weight), and zinc salts (about 1% by weight) to said individual, wherein the composition does not comprise a peptide, polypeptide or protein and the composition is free of aluminum or aluminum ions, and wherein the composition reduces redness by at least about 27% in said individual about 2 weeks after administration of said composition.

6. The method of claim 5, wherein the dextran sulfate is dextran sodium sulfate.

7. The method of claim 5, wherein the dextran sulfate has a molecular weight of at least 100 g per mol.

8. The method of claim 5, wherein the dextran sulfate has a molecular weight of between 100 to 100,000 g per mol.

9. The method of claim 8, wherein the dextran sulfate has a molecular weight of between 100 to 25,000 g per mol.

10. The method of claim 9, wherein the dextran sulfate has a molecular weight of between 100 to 10,000 g per mol.

11. The method of claim 5, wherein the composition is formulated as a solution, suspension, gel, hydrogel, cream, emulsion, micro-emulsion, nano-emulsion, lotion, spray, ointment, patch, tissue cloth, wipe, soap, paste, aerosol, or mask suitable for topical use.

12. The method of claim 5, wherein the composition is free of cationic polymers selected from the group consisting of chitosan, DEAE-dextran, cationic guar gum, cationic polysaccharides, cationic celluloses, cationic copolymers of saccharides and synthetic cationic monomers, cationic polyakylene imines, and cationic ethoxy polyalkylene imines.

13. The method of claim 5, further comprising administering one or more additional compounds or active ingredients selected from the group consisting of rosacea inhibitory agents; $\alpha$-adrenergic receptor agonists; chemicals or botanical extracts with vasoconstrictor properties; nasal decongestants, sinus decongestants, or combinations thereof; chemicals or botanical extracts with anti-inflammatory properties; chemicals or botanical extracts with antihistamine properties; chemicals or botanical extracts with anti-microbial properties; chemicals or botanical extracts with anti-fungal properties; chemicals or botanical extracts with anti-mite properties; chemicals or botanical extracts with anti-acne properties; chemicals or botanical extracts with anti-parasitic properties; chemicals or botanical extracts with anti-dandruff properties; chemicals or botanical extracts with anti-seborrheic properties; keratolytic agents or botanical extracts with keratolytic properties; chemicals or botanical extracts with anti-androgen properties; chemicals or botanical extracts with astringent properties; serine protease inhibitors; saturated dicarboxylic acids; alpha hydroxy acids; and beta hydroxy acids; retinoic acid, tretinoin, isotretinoin, adapalene, retinol, or derivatives thereof; benzoyl peroxide; dapsone; kinetin ($N^6$-furfuryladenine) and derivatives thereof such as furfurylaminotetrahydropyranyladenine; niacinamide (nicotinamide); sunscreens; antioxidants; emollients; humectants; skin protectants; skin barrier enhancers; skin penetration enhancers; minerals suitable for cosmetic use; make-up suitable for cosmetic use; optical blurring agents suitable for cosmetic use; ingredients stimulating epidermal or other stem cells; skin conditioning agents; skin lightening agents, skin brightening agents, or combinations thereof; anti-wrinkle agents, anti-aging agents, or combinations thereof; plant or vegetable extracts; vegetable oils; silicon oils; fatty acids, fatty acid esters, or combinations thereof; and any mixtures or combinations thereof.

14. The method of claim 13, wherein the rosacea inhibitory agents are selected from the group consisting of metronidazole, sulfacetamide, sodium sulfacetamide, sulfur, dapsone, doxycycline, minocycline, clindamycin, clindamycin phosphate, erythromycin, tetracylines, and azelaic acid, calcium dobesilate, maleic acid; and any compatible combinations thereof.

15. The method of claim 13, wherein the $\alpha$-adrenergic receptor agonists are selected from the group consisting of clonidine, amphetamine, doxtroamphetamine, apraclonidine, dipivefrin, $\alpha$-methyldopa, oxymetazoline, oxymetazoline hydrochloride, methoxamine, metaraminol, medetomidine, dexmedetomidine, ethylnorepinephrine, guanfacine, guanabenz, phenylephrine, phenylephrine hydrochloride, ephedrine, epinine, epinephrine, ethylnorepinephrine, levarterenol, lofexidine, norepinephrine, norphenylephrine, norephedrine, phenylpropanolamine, pemoline, propylhexadrine, pseudoephedrine, methamphetamine, $\alpha$-methylnorepinephrine, methylphenidate, mephentermine, midodrine, mivazerol, moxonidine, desglymidodrine, tetrahydrozoline, tetrahydrozoline hydrochloride, cirazoline, amidephrine, brimonidine, brimonidine tartrate, naphazoline, isoproterenol, xylazine, xylometazoline, and tizanidine.

16. The method of claim 13, wherein the chemicals or botanical extracts with vasoconstrictor properties are selected from the group consisting of corticosteroids, ephedrine, pseudoephedrine, caffeine, escin; ephedra, phedra sinica, hamamelis viginiana, hydrastis canadensis, lycopus virginicus, aspidosperma quebracho, cytisus scoparius, raphanus sativus linn (radish leave extracts), horse chestnut extract; and any compatible combinations thereof.

17. The method of claim 13, wherein the chemicals or botanical extracts with anti-inflammatory properties are selected from the group consisting of corticosteroids (for short term use), non-steroidal anti-inflammatory drugs, linoleic acid, linolenic acid, bisabolol, glycyrrhetinic acid, glycerin, plant extracts with anti-inflammatory properties such as tea extracts, anti-inflammatory interleukins such as Il-1ra, isoprenylcystein analogues such as N-acetyl-S-farnesyl-L-cysteine, aromatic aldehydes with anti-inflammatory properties such as 4-ethoxy benzaldehyde, and any compatible combinations thereof.

18. The method of claim 13, wherein the chemicals or botanical extracts with anti-microbial properties are antibiotics selected from the group consisting of gentamicin, penicillins, cephalosporins, quinolones, ciprofloxacin, novobiocin, and combinations thereof.

19. The method of claim 13, wherein the chemicals or botanical extracts with anti-fungal properties are selected from the group consisting of ketoconazole, naftifine hydrochloride, oxiconazole nitrate, sulconazole nitrate, urea, terbinafine hydrochloride, and selenium sulfide.

20. The method of claim 13, wherein the chemicals or botanical extracts with anti-acne properties are selected from the group consisting of benzoyl peroxide, salicylic acid, retinoic acid, tretinoin; alpha-hydroxy acids; and antibiotics.

21. The method of claim 13, wherein the keratolytic agents or botanical extracts with keratolytic properties are selected from the group consisting of alpha-hydroxy acids, beta-hydroxy acids, polyhydroxy acids, urea, and salicylic acid.

22. The method of claim 13, wherein the alpha hydroxy acids are selected from the group consisting of glycolic acids, lactic acid, malic acid, citric acid, and tartaric acid.

23. The method of claim 13, wherein the beta hydroxy acids are selected from the group consisting of carnitine, 3-hydroxybutyric acid, 3-hydroxypropionic acid, β-hydroxy 3-methylbutyric acid, and salicylic acid.

24. The method of claim 13, wherein the minerals suitable for cosmetic use are selected from the group consisting of talc, mica, and iron oxides.

25. The method of claim 13, wherein the phospholipids are selected from the group consisting of phosphatidylcholines, lysophosphatidylcholines, lecithins, and lysolecithins.

26. The method of claim 13, wherein the growth factors or cytokines are selected from the group consisting of TGF-betas, EGF, PDGF, processed skin cell proteins (PSP®), Nouricel-MD®, cell lysates such as fibroblast cell lysate, and conditioned cell culture mediums.

27. The method of claim 13, wherein the plant or vegetable extracts are selected from the group consisting of extracts or concentrates such as lyophilisates, evaporates, and distillates from yeast; brewer spent grain (byproduct of beer brewing); barley; soybean; soybean milk; oat; lavender; licorice; ginger; ginseng; turmeric; apple; sea whip; algae; aloe vera (barbadensis) leaves; tea; chamomile; and birch tree.

28. The method of claim 13, wherein the fatty acid or fatty acid esters are selected from the group consisting of linoleic acid, linolenic acid, and esters thereof.

29. The method of claim 5, further comprising administering one or more of metronidazole, sulfacetamide, sodium sulfacetamide, sulfur, tetracylines, doxycycline, clindamycin, clindamycin phosphate, erythromycin, minocycline, and combinations thereof.

30. The method of claim 5, further comprising administering azelaic acid, theobromine, theophylline, xanthines, glycerin, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, creatine, carnitine, essential fatty acids including linoleic acid and linolenic acid, copper salts, or any combinations thereof.

31. The method of claim 5, wherein the zinc salts are selected from the group consisting of such as, for example, zinc sulfate, zinc chloride, zinc glycinate, zinc gluconate, zinc-histidine, zinc L-2-pyrrolidone-5-carboxylate (zinc PCA), zinc salt of linoleic acid, zinc salt of linolenic acid, zinc salt of azelaic acid, zinc oxide, and combinations thereof.

32. The method of claim 30, wherein the copper salts are selected from the group consisting of copper sulfate, copper chloride, copper glycinate, copper gluconate, copper-histidine, copper L-2-pyrrolidone-5-carboxylate (copper PCA), copper salt of linoleic acid, copper salt of linolenic acid, copper salt of azelaic acid, copper peptides, and combinations thereof.

33. The method of claim 5, wherein the individual has elevated levels of cathelicidin in the skin or on the skin surface as compared to normal skin.

34. The method of claim 5, wherein the individual has elevated levels of defensins in the skin or on the skin surface as compared to normal skin.

35. The method of claim 5, wherein the composition is administered to the individual in an amount, administered dose, frequency of administration, and duration of treatment that is suitable for the individual and is sufficient to cause a decrease in one or more symptoms associated with rosacea, psoriasis, acne, atopic dermatitis and/or seborrheic dermatitis.

36. The method of claim 35, wherein the administered dose onto the surface of the skin is 0.2 to 2 mg of the composition per $cm^2$.

37. The method of claim 35, wherein the frequency of administration is daily, twice daily, three times daily, once weekly, or twice weekly.

38. The method of claim 35, wherein the duration of treatment is for at least one to two weeks.

\* \* \* \* \*